US012780889B2

(12) United States Patent
Paciotti

(10) Patent No.: US 12,780,889 B2
(45) Date of Patent: Nov. 3, 2026

(54) CYTOKINE COMPOSITIONS AND METHODS OF USE THEREOF

(71) Applicant: Zahav Bioscience LLC, Philadelphia, PA (US)

(72) Inventor: Giulio Franco Paciotti, Columbia, MD (US)

(73) Assignee: Zahav Bioscience LLC

( * ) Notice: Subject to any disclaimer, the term of this patent is extended or adjusted under 35 U.S.C. 154(b) by 0 days.

(21) Appl. No.: 19/254,656

(22) Filed: Jun. 30, 2025

(65) Prior Publication Data

US 2025/0326810 A1 Oct. 23, 2025

Related U.S. Application Data

(63) Continuation of application No. 18/358,510, filed on Jul. 25, 2023.

(51) Int. Cl.

| | |
|---|---|
| ***C07K 14/525*** | (2006.01) |
| ***A61K 47/02*** | (2006.01) |
| ***A61K 47/10*** | (2017.01) |
| ***A61P 37/02*** | (2006.01) |
| ***B82Y 5/00*** | (2011.01) |
| ***C07K 14/54*** | (2006.01) |
| ***C07K 14/57*** | (2006.01) |

(52) U.S. Cl.

CPC ............ *C07K 14/525* (2013.01); *A61K 47/02* (2013.01); *A61K 47/10* (2013.01); *A61P 37/02* (2018.01); *B82Y 5/00* (2013.01); *C07K 14/5434* (2013.01); *C07K 14/57* (2013.01)

(58) Field of Classification Search

CPC ......... B82Y 5/00; C07K 14/525; C07K 14/57

See application file for complete search history.

(56) References Cited

U.S. PATENT DOCUMENTS

| | | | |
|---|---|---|---|
| 7,387,900 | B2 | 6/2008 | Tamarkin et al. |
| 7,790,167 | B2 | 9/2010 | Tamarkin et al. |
| 7,951,614 | B2 | 5/2011 | Tamarkin et al. |
| 7,960,145 | B2 | 6/2011 | Paciotti et al. |
| RE42,524 | E | 7/2011 | Tamarkin et al. |
| 8,033,977 | B2 | 10/2011 | Hainfeld et al. |
| 8,080,183 | B2 | 12/2011 | Kotov et al. |
| 8,309,135 | B2 | 11/2012 | Chen et al. |
| 8,435,801 | B2 | 5/2013 | Tamarkin et al. |
| 8,486,663 | B2 | 7/2013 | Paciotti et al. |
| 8,486,666 | B2 | 7/2013 | Schildkraut |
| 8,785,202 | B2 | 7/2014 | Tamarkin et al. |
| 9,056,129 | B2 | 6/2015 | Hanson et al. |
| 9,095,613 | B2 | 8/2015 | Choi et al. |
| 9,095,625 | B2 | 8/2015 | Bogdanov |
| 9,393,396 | B2 | 7/2016 | Peyman |
| 9,561,289 | B2 | 2/2017 | Corti et al. |
| 9,683,032 | B2 | 6/2017 | Klingelhöfer et al. |
| 9,845,237 | B2 | 12/2017 | Tseng et al. |
| 10,137,208 | B2 | 11/2018 | Qian et al. |
| 10,398,784 | B2 | 9/2019 | Mirkin et al. |
| 10,835,604 | B2 | 11/2020 | Ngwa et al. |
| 11,045,548 | B2 | 6/2021 | El-Sayed et al. |
| 11,065,202 | B2 | 7/2021 | Karathanasis et al. |
| 11,179,344 | B2 | 11/2021 | Coulter et al. |
| 11,266,746 | B2 | 3/2022 | Oppenheim et al. |
| 11,369,425 | B2 | 6/2022 | Lee et al. |
| 11,660,229 | B2 | 5/2023 | Peyman |
| 11,896,681 | B2 | 2/2024 | Jon et al. |
| 12,116,603 | B2 | 10/2024 | Cao et al. |
| 12,178,889 | B2 | 12/2024 | Harrison, Jr. et al. |
| 2006/0222595 | A1 | 10/2006 | Mukherjee et al. |
| 2009/0148535 | A1 | 6/2009 | Bamdad |
| 2010/0028261 | A1 | 2/2010 | Emelianov et al. |
| 2011/0077581 | A1 | 3/2011 | Oyelere et al. |
| 2011/0111002 | A1 | 5/2011 | Pop |
| 2012/0046593 | A1 | 2/2012 | Oraevsky et al. |
| 2013/0023714 | A1 | 1/2013 | Johnston et al. |
| 2013/0225901 | A1 | 8/2013 | Krishnan et al. |
| 2013/0336924 | A1 | 12/2013 | Alvarez et al. |
| 2014/0008301 | A1 | 1/2014 | Ostafin et al. |
| 2014/0086828 | A1 | 3/2014 | Foster et al. |
| 2014/0128451 | A1 | 5/2014 | Gunaratne et al. |
| 2016/0243254 | A1 | 8/2016 | Artzi et al. |
| 2016/0250352 | A1 | 9/2016 | Mo et al. |
| 2016/0258940 | A1 | 9/2016 | Ichikawa et al. |

(Continued)

FOREIGN PATENT DOCUMENTS

| | | | |
|---|---|---|---|
| AU | 2014240352 | A1 | 10/2014 |
| EP | 2242539 | B1 | 10/2010 |

(Continued)

OTHER PUBLICATIONS

Punta et al. The Rough Guide to in Silico Function Prediction, or How to Use Sequence and Structure Information to Predict Protein Function. PLoS Comput Biol 4(10): e1000160, 2008 (Year: 2008).*

Whisstock et al. (Quarterly Reviews in Biophysics. 36(3):307-340, 2007 (Year: 2007).*

Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*

Song et al. A Single Amino Acid Change (Asp 533Ala53) Converts Survivin from Anti-apoptotic to Pro-apoptotic. Molecular Biology of the Cell, 15:1287-1296, Mar. 2004 (Year: 2004).*

(Continued)

*Primary Examiner* — Vanessa L. Ford

*Assistant Examiner* — Sandra Carter

(74) *Attorney, Agent, or Firm* — Bookoff McAndrews, PLLC

(57) ABSTRACT

Provided herein are novel constructs comprising gold nanoparticles bound to two types of cytokines, wherein the two types of cytokines comprise Tumor Necrosis Factor alpha (TNFα) and a cytokine selected from the group consisting of Interferon gamma (IFNγ) and Interleukin-12.

20 Claims, 30 Drawing Sheets

(56) References Cited

U.S. PATENT DOCUMENTS

| | | | |
|---|---|---|---|
| 2017/0202976 | A1 | 7/2017 | Onur et al. |
| 2018/0008551 | A1 | 1/2018 | Kannan et al. |
| 2018/0009036 | A1 | 1/2018 | Mao et al. |
| 2018/0133319 | A1 | 5/2018 | Vo-Dinh et al. |
| 2018/0133343 | A1 | 5/2018 | Irvine et al. |
| 2018/0250404 | A1 | 9/2018 | Krishnan et al. |
| 2018/0250420 | A1 | 9/2018 | Kannan et al. |
| 2018/0271788 | A1 | 9/2018 | Chen et al. |
| 2018/0303937 | A1 | 10/2018 | Da Silva Ferreira et al. |
| 2019/0008965 | A1 | 1/2019 | Messersmith et al. |
| 2019/0142966 | A1 | 5/2019 | Artzi et al. |
| 2019/0185854 | A1 | 6/2019 | Artzi et al. |
| 2020/0246484 | A1 | 8/2020 | Mirkin et al. |
| 2020/0355694 | A1 | 11/2020 | Aimiya et al. |
| 2021/0196750 | A1 | 7/2021 | Vivas-Mejia et al. |
| 2021/0338717 | A1 | 11/2021 | Ouyang et al. |
| 2022/0008451 | A1 | 1/2022 | Paleni et al. |
| 2022/0025403 | A1 | 1/2022 | Adair et al. |
| 2022/0160892 | A1 | 5/2022 | Li et al. |
| 2022/0241439 | A1 | 8/2022 | Zheng et al. |
| 2022/0401576 | A1 | 12/2022 | Lin et al. |
| 2023/0000999 | A1 | 1/2023 | Parang et al. |
| 2023/0181769 | A1 | 6/2023 | Allen et al. |
| 2023/0285457 | A1 | 9/2023 | Daneri Navarro et al. |
| 2024/0218371 | A1 | 7/2024 | Chin et al. |
| 2024/0293561 | A1 | 9/2024 | Popovtzer et al. |
| 2024/0301431 | A1 | 9/2024 | Kim et al. |
| 2024/0350828 | A1 | 10/2024 | Akhter et al. |
| 2024/0398976 | A1 | 12/2024 | Saxena et al. |
| 2025/0000876 | A1 | 1/2025 | Khang et al. |
| 2025/0009866 | A1 | 1/2025 | Kotov et al. |

FOREIGN PATENT DOCUMENTS

| | | | | |
|---|---|---|---|---|
| EP | 2403539 | A2 | 1/2012 | |
| EP | 2451481 | B1 | 5/2012 | |
| EP | 2706354 | A1 | 3/2014 | |
| EP | 2953646 | A | 12/2015 | |
| EP | 3463316 | A2 | 4/2019 | |
| EP | 4525917 | A1 | 3/2025 | |
| WO | 9924077 | A2 | 5/1999 | |
| WO | WO-2009039502 | A1 * | 3/2009 | .............. A61P 43/00 |
| WO | 2009062151 | A1 | 5/2009 | |
| WO | 2010101627 | A2 | 9/2010 | |
| WO | WO-2012039685 | A1 * | 3/2012 | ............. B82Y 40/00 |
| WO | 2013042125 | A2 | 3/2013 | |
| WO | 2013043591 | A1 | 3/2013 | |
| WO | 2014123935 | A1 | 8/2014 | |
| WO | 2017012591 | A1 | 1/2017 | |
| WO | 2017210666 | A2 | 12/2017 | |
| WO | 2018045058 | A1 | 3/2018 | |
| WO | 2018207115 | A1 | 11/2018 | |
| WO | 2022165260 | A1 | 8/2022 | |
| WO | 2023223307 | A1 | 11/2023 | |
| WO | 2024020366 | A1 | 1/2024 | |
| WO | 2024068099 | A1 | 4/2024 | |
| WO | 2024170884 | A1 | 8/2024 | |
| WO | 2025006911 | A1 | 1/2025 | |
| WO | 2025043210 | A1 | 2/2025 | |
| WO | 2025046399 | A1 | 3/2025 | |

OTHER PUBLICATIONS

Defeo-Jones et al. Substitution of Lysine for Arginine at Position 42 of Human Transforming Growth Factor-a Eliminates Biological Activity without Changing Internal Disulfide Bonds. Molecular and Cellular Biology, Sep. 1989, p. 4083-4086 (Year: 1989).*

Bork. Powers and Pitfalls in Sequence Analysis: The 70% Hurdle. Genome Research, 2000; 10:398-400 (Year: 2000).*

Corti et al. Enhancement of doxorubicin anti-cancer activity by vascular targeting using IsoDGR/cytokine-coated nanogold. J. Nanobiotechnol, 2021, 19:128 (Year: 2021).*

Liu et al. Thiol-ene click chemistry: a biocompatible way for orthogonal bioconjugation of colloidal nanoparticles. Chem Sci. Jun. 22, 2017;8(9):6182-6187 (Year: 2017).*

Paciotti et al. Cancer Res (2005) 65 (9_Supplement): 337-338 (Year: 2005).*

Alexander et al., "Tumor Necrosis Factor: Basic Principles and clinical applications in systemic and regional cancer treatment", Principles and Practice of the Biologic Therapy of Cancer, 2000, Eds. S. Rosenberg, Lippincott Williams and Wilkins, pp. 174-193.

Angell et al., "MHC Class I Loss Is a Frequent Mechanism of Immune Escape in Papillary Thyroid Cancer That Is Reversed by Interferon and Selumetinib Treatment In Vitro", Clinical Cancer Research, vol. 20, No. 23, 2014, pp. 6034-6044.

Corti et al., "Enhancement of doxorubicin anti-cancer activity by vascular targeting using IsoDGR/cytokine-coated nanogold", Journal of Nanobiotechnology, 2021, vol. 19, No. 128, pp. 1-13.

Emens, "Chemotherapy and tumor immunity: an unexpected collaboration", Front Biosci., 2011, vol. 13, pp. 249-257.

Farma et al., "Direct evidence for rapid and selective induction of tumor neovascular permeability by tumor necrosis factor and a novel derivative, colloidal gold bound tumor necrosis factor", International Journal of Cancer, 2007, vol. 120, No. 11, pp. 2474-2480.

Fraker, "Treatment of patients with melanoma of the extremity using hyperthermic isolated limb perfusion with melphalan, tumor necrosis factor, and interferon gamma: results of a tumor necrosis factor dose-escalation study", Journal of Clinical Oncology, 1996, vol. 14, No. 2, pp. 479-489.

Millipore Sigma, "FTC-133 Cell Line human", pp. 1-8, available at: https://www.sigmaaldrich.com/US/en/product/sigma/94060901gclid=Cj0KCQjwn_OIBhDhARIsAG2y6zNTb7BKWDWPBO6I6OjVUjNF0Vus40EnabHKjdser6KPxowvAzmFegaAiSFEALw_wcB&gclsrc=aw.ds (last accessed Mar. 27, 2025).

Ichikawa et al., "Cardiotoxicity of doxorubicin is mediated through mitochondrial iron accumulation", The Journal of Clinical Investigation, 2014, vol. 124, No. 2, pp. 617-630.

International Search Report mailed Feb. 14, 2024 for International Patent Application No. PCT/US2023/070940 filed on Jul. 25, 2023, pp. 1-4.

Koonce et al., "Combination of Gold Nanoparticle-Conjugated Tumor Necrosis Factor-α and Radiation Therapy Results in a Synergistic Antitumor Response in Murine Carcinoma Models", International Journal of Radiation Oncology* Biology* Physics, 2015, vol. 93, No. 3, pp. 588-596.

Lavi et al., "Tumor necrosis factor induces expression of MHC class I antigens on mouse astrocytes", Journal of Neuroimmunology, 1988, vol. 18, pp. 245-253.

Libutti et al., "Phase I and Pharmacokinetic Studies of CYT-6091, a Novel PEGylated Colloidal Gold-rhTNF Nanomedicine", Clinical Cancer Research, 2010, vol. 16, No. 24, pp. 6139-6149.

Lode et al., "Tumor-targeted IL-2 amplifies T cell-mediated immune response induced by gene therapy with single-chain IL-12", PNAS, 1999, vol. 96, pp. 8591-8596.

Nagarajan et al., "Glycolipid-anchored IL-12 Expressed on Tumor Cell Surface Induces Antitumor Immune Response", Cancer Research, 2002, vol. 62, No. 10, pp. 2869-2874.

Ning et al., "The prospect of immunotherapy combined with chemotherapy in patients with advanced non-small cell lung cancer: a narrative review", Annals of Translational Medicine, vol. 9, No. 22, pp. 1-7.

Paciotti et al., "Colloidal Gold: A Novel Nanoparticle Vector for Tumor Directed Drug Delivery", Drug Delivery, 2004, vol. 11, pp. 169-183.

Paciotti et al., "Synthesis and Evaluation of Paclitaxel-Loaded Gold Nanoparticles for Tumor-Targeted Drug Delivery", Bioconjugate Chemistry, 2016, vol. 27, No. 11, pp. 2646-2657.

Pfreundschuh et al., "Phase I Study of Intratumoral Application of Recombinant Human Tumor Necrosis Factor", European Journal Cancer Clinical Oncology, 1989, vol. 25, No. 2, pp. 379-388.

Tamarkin et al., "Cancer nanomedicines: Opportunities and challenges", 11th Annual TechConnect World Innovation Conference and Expo, Held Jointly with the 20th Annual Nanotech Conference and Expo, and the 2017 National SBIR/STTR Conference, TechConnect Briefs, 2017, pp. 126-129.

(56) References Cited

OTHER PUBLICATIONS

Zhou, "Molecular Mechanisms of IFN-gamma to Up-Regulate MHC Class I Antigen Processing and Presentation", International Reviews of Immunology, 2009, vol. 28, Nos. 3-4, pp. 239-260.
Zhu et al., "Combination strategies to maximize the benefits of cancer immunotherapy", Journal of Hematology & Oncology, 2021, vol. 14, No. 156, pp. 1-33.
Zitvogel et al., "Immunological aspects of cancer chemotherapy", Nature Reviews Immunology, vol. 8, pp. 59-73.
Paciotti et al., "AuriTax: tumor targeted paclitaxel delivery by TNF bound to colloidal gold nanoparticles", Cancer Res., 2005, pp. 337-338, vol. 65, issue No. 9_Supplement.
Pretto et al., "Preclinical evaluation of IL2-based immunocytokines supports their use in combination with dacarbazine, paclitaxel and TNF-based immunotherapy", Cancer Immunol Immunother., 2014, pp. 901-910, vol. 63.

* cited by examiner

Concentration of CYT-IFNγ: IFNγ = 1,000 ng; TNFα = 50 ng

CYT-mIFNγ-TNFα-induced MHC-1 expression stimulates the proliferation of naïve splenocytes on the surface of cancer cells.

CYTOKINE COMPOSITIONS AND METHODS OF USE THEREOF

CROSS-REFERENCE TO RELATED APPLICATIONS

This application is a continuation of and claims the benefit of priority to U.S. patent application Ser. No. 18/358,510, filed Jul. 25, 2023, the entirety of which is incorporated herein by reference.

TECHNICAL FIELD

Embodiments of this disclosure relate generally to novel nanoparticle and cytokine compositions, and constructs and to methods for making and using the same.

BACKGROUND OF THE INVENTION

Focused delivery of therapeutic agents to targeted areas of the body, without diminishing the potency or efficacy of such therapeutic agents, would allow for the improvement of treatment regimens. For example, current treatments for cancer include administration of chemotherapeutic agents and other biologically active factors such as cytokines and immune factors that impact the entire organism. The side effects of non-specific delivery include organ damage, loss of senses such as taste and feeling, as well as hair loss. While such currently available therapies provide treatment for a particular condition, they also require adjunct therapies to treat resulting side effects.

Formulations comprising therapeutic payloads having potentially toxic side-effects when administered systemically, would benefit from technological advancements that improve site-specific delivery and the stability of the formulations while diminishing the indiscriminate release of the payload, and thereby improve the overall therapeutic effect of the drug.

An additional deficiency of currently available treatments relates to ability to preserve or increase the potency of the therapeutic agents being administered. While delivering such agents to the site of a disease such as a tumor is a priority, it is also important to preserve the activity of such agents such that they are able to have maximum effect.

What is needed are compositions and methods for delivery systems of agents that affect the desired cells or site, while preserving or improving the therapeutic efficacy of such agents. Such systems may be used for delivery to specific cells of agents of all types. What is also needed are delivery systems that facilitate the targeted delivery of the therapeutic payload and do not cause unwanted side effects in the entire organism.

SUMMARY OF THE INVENTION

In an embodiment, the present disclosure relates to compositions and methods related to constructs comprising colloidal gold particles and cytokines, optionally combined with one or more therapeutic agents, one or more polyethylene glycol molecules. In certain embodiments, the colloidal gold particles comprise nanoparticles, and in certain embodiments the nanoparticles consist of colloidal gold nanoparticles. In certain embodiments, the gold nanoparticles are bound to two types of cytokines, either Tumor Necrosis Factor alpha (TNFα) (1) and interferon gamma (IFNγ), TNFα and Interleukin-2 (IL-2) (2) or TNFα and Interleukin-12 (IL-12) (3). The polyethylene glycol molecules may comprise a polyethylene glycol derivative covalently bound to the colloidal gold nanoparticle.

BRIEF DESCRIPTION OF FIGURES

The present disclosure is best understood from the following detailed description when read in conjunction with the accompanying drawings. It is emphasized that, according to common practice, the various features of the drawings are not necessarily to scale. On the contrary, the dimensions of the various features are arbitrarily expanded or reduced for clarity. Like reference numerals denote like features throughout specification and drawings.

FIG. 3A shows untreated cells. FIGS. 3B & 3C show localization of the nanoparticle 45 minutes (FIG. 3B) and 8 hours (FIG. 3C) after addition of the nanoparticle.

FIG. 4B)); CYT-INFγ (IFNγ single agent; FIG. 4C); and CYT-IFNγ-TNFα (FIG. 4D). The cells were cultured for an additional 5-7 days, and cytotoxicity was assessed by microscopy.

FIGS. 9A-9S provide micrographs demonstrating the induction of HLA-A-C in human cancer cell lines treated with CYT-IFNγ-TNFα. 20,000 FTC-133, H-460 or A549 cells were plated in 6 well tissue culture clusters. 48 hours after plating the cells received various doses of CYT-IFNγ-TNFα (for experimental details refer to Examples section below, in particular Example 3). FIG. 9 provides three pictures of control wells and six pictures of CYT-IFNγ-TNFα treated wells. FIGS. 9A-9C demonstrate the induction of HLA-A-C by 1 μg of CYT-IFNγ-TNFα in FTC-133 cells. FIGS. 9L-9O and 9P-9S illustrate the uptake and intracellular processing of CYT-IFNγ-TNFα by A549 lung cancer cells. Consistent with the observations discussed herein, CYT-IFNγ-TNFα induced the expression of HLA-A-C by A549 cells.

FIGS. 10A-10D provide micrographs showing splenocyte activation induced by treating murine cancer cells with CYT-IFNγ-TNFα. FIGS. 10A-10B illustrate the proliferation of naïve splenocytes, isolated from naïve Balb/c mice, induced by Colo 26 cancer cells treated with CYT-mIFNγ-TNFα. Note that in the control (untreated) cell co-culture the splenocytes, though resting on the surface of the cancer cells, did not proliferate. FIGS. 10C-10D illustrate the early and later stage proliferation of naïve splenocytes, isolated from naïve C57Bl/6 mice, induced by B16F10 melanoma cancer cells treated with CYT-m-IFNγ-hTNFα.

FIG. 13A depicts a control animal (no injection) at T=3.5 H post injection. FIG. 13B provides an image taken 3.5 hours after an intravenous injection of CYT-mIFNg-hTNFα.

DETAILED DESCRIPTION

Figure 1:
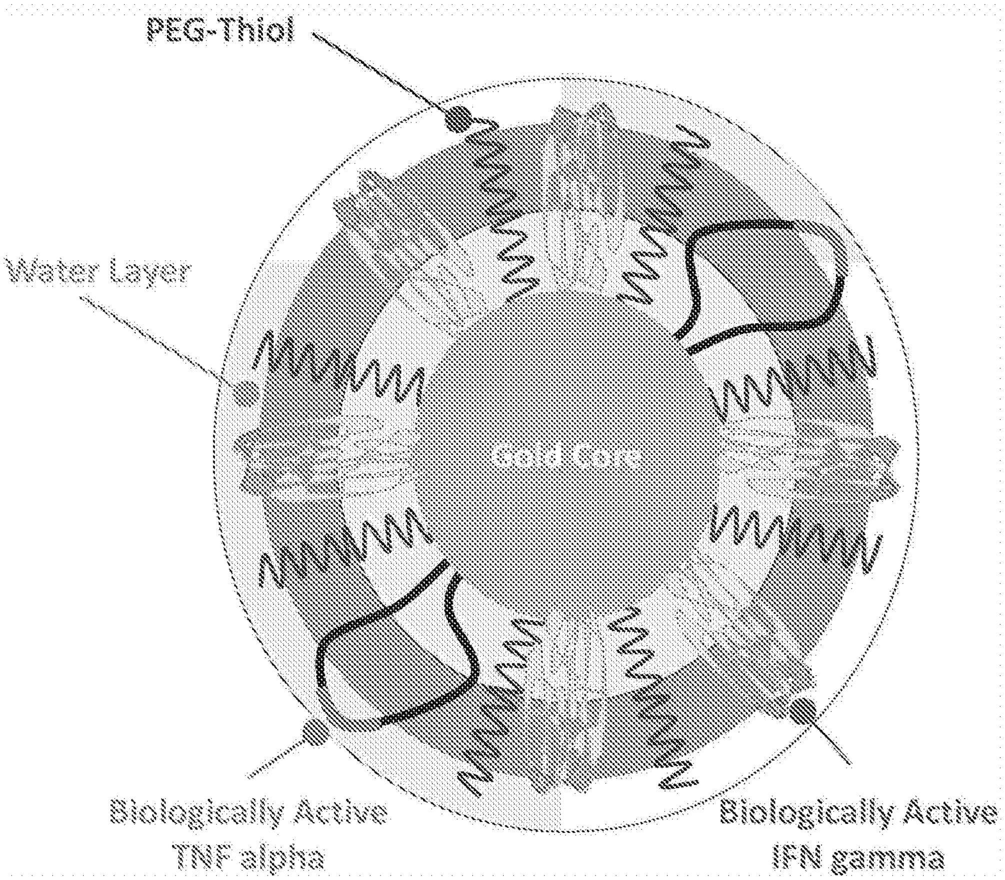
FIG. 1 provides a schematic of the CYT-IFNγ-TNFα nanoparticle.

The following detailed description is exemplary and explanatory and is intended to provide further explanation of the present disclosure described herein. Other advantages, and novel features will be readily apparent to those skilled in the art from the following detailed description of the present disclosure. Texts and references mentioned herein are incorporated in their entirety, including U.S. Pat. Nos. 7,387,900, 7,790,167, 7,951,614, 7,960,145, RE42524, 8,435,801, 8,486,666, and 8,785,202.

As used herein, the term "subject" should be construed to include subjects, for example medical or surgical subjects, such as humans and other animals requiring therapeutic intervention.

In the present disclosure the singular forms "a," "an," and "the" include the plural reference, and reference to a particular numerical value includes at least that particular value, unless the context clearly indicates otherwise. Thus, for example, a reference to "a bead" or "a nano structure" is a reference to one or more of such structures and equivalents thereof known to those skilled in the art, and so forth. When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive; as another example, the phrase "about 8%" preferably (but not always) refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", "2-5", and the like. In addition, when a list of alternatives is positively provided, such a listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." It is intended that any component, element, attribute, or step that is positively recited herein may be explicitly excluded in the claims, whether such components, elements, attributes, or steps are listed as alternatives or whether they are recited in isolation.

The term "cytokine" as used herein refers to a broad class of small proteins such as interferon, interleukin, and growth factors, which are secreted by certain cells of the immune system and have an effect on other cells. Cytokines in this disclosure include interferon gamma (IFNγ), TNFα, interleukin-2 (IL-2), and interleukin-12 (IL-12).

The term "cytotoxicity" as used herein refers to the degree to which a substance can cause damage to a cell. A substance or process that causes cell damage or death is referred to as cytotoxic. Treating cells with the cytotoxic compound can result in a variety of cell fates. Cells may undergo apoptosis or necrosis, in which they lose membrane integrity and die rapidly as a result of cell lysis. Cells can also stop actively growing and dividing (leading to a decrease in cell viability), or the cells can activate pathway-controlled cell death (i.e., apoptosis).

The term "paclitaxel" as used herein refers to a type of chemotherapy drug that is used to treat cancer. Paclitaxel is a taxane chemotherapeutic. A "paclitaxel prodrug" comprises a compound with little or no pharmacological activity that converts into a pharmacologically active paclitaxel drug compound in an area of interest in vivo. Such a prodrug may comprise a thiol derivatized paclitaxel prodrug.

For purposes of the description hereinafter, it is to be understood that the embodiments described below may assume alternative variations and embodiments. It is also to be understood that the specific articles, compositions, and/or processes described herein are exemplary and should not be considered as limiting.

Tumor necrosis factor alpha (TNFα) (1) is a pleiotropic cytokine that impacts nearly every aspect of human health. Its discovery in the 1970s had profound implications for treating solid tumors as a single injection of the protein resulted in hemorrhagic necrosis of solid tumors regardless of whether the cancer cells were sensitive to the protein. With continued research, TNFα has been found to selectively destroy the tumor vasculature (5), reduce tumor interstitial fluid pressure (6), increase the uptake of follow-on chemotherapy (7), and recruit immune system cells to the site of the tumor. Collectively, these effects may result in significant anti-tumor responses.

Not long after its discovery a recombinant form of the cytokine was produced to support clinical trials in cancer patients. Unfortunately, in nearly 200 clinical trials, systemically delivered TNFα was shown to be highly toxic and thus limited the dose that could safely be administered to cancer patients. The major dose-limiting toxicity of TNFα is hypotension and hepatoxicity (6). In all of these clinical trials no durable anti-tumor responses were observed.

Moreover, it was discovered in early phase 1 clinical trials of TNFα that many of the potentially dangerous side effects caused by TNFα occur at even low doses. Some of these, including severe fever and chills, can be pharmaceutically controlled, and therefore do not represent significant barriers to patient treatment or compliance with treatment. Other adverse effects such as tachycardia are potentially disqualifying AEs (8). This condition can lead to stroke and heart attack in at-risk patients. Notably, many cancer therapies, such as doxorubicin (9), which might be given in combination with CYT-6091 (described below), are known to be cardiotoxic.

Given these data, the use of TNFα in cancer treatment has been relegated to a limb-sparing procedure known as Isolated Limb Perfusion (ILP) (10). In the procedure, patients presenting with melanoma or sarcoma on their extremities will have the blood vessels of the affected limb connected to a heart-lung machine that perfuses the limb with TNFα followed by chemotherapy through the limb. ILP achieves two major goals: first, the localized delivery of TNF increases the concentration of the cytokine at the site of disease; secondly, the regional perfusion of the cytokine within the limb reduces systemic exposure to the cytokine and thus avoids most of the toxic side effect. However, the remarkable anti-tumor responses (60-75% complete and durable (10-years)) led the inventor to the development of the first patented gold nanoparticle, CYT-6091.

CYT-6091 (11-12) is comprised of a 27 nm gold nanoparticle that is covalently linked, via the formation of coordinate covalent bonds, with TNFα and PEG-THIOL.

Novel cytokine constructs comprising gold nanoparticles and TNFα are disclosed herein. In an embodiment, provided herein are constructs comprising gold nanoparticles bound to two types of cytokines, wherein the two types of cytokines comprise Tumor Necrosis Factor alpha (TNFα) and a cytokine selected from the group consisting of Interferon gamma (IFNγ) and Interleukin-12 (IL-12) or Interleukin-2 (IL-2). One embodiment consists of a gold nanoparticle bound to TNFα and IFNγ, and in certain embodiments, the ratio of TNFα to IFNγ is about 20:1 (w/w). Another embodiment consists of a gold nanoparticle bound to TNFα and Interleukin-2 (IL-2) or TNFα and Interleukin-12 (IL-12).

In certain embodiments the cytokine constructs of the disclosure comprise cytokines that may be bound to the surface of the gold nanoparticles using one or more binding chemistries including thiol or other covalent binding, ionic binding, or hydrophobic interactions.

In certain embodiments, the cytokine constructs may further comprise polyethylene glycol, polyethylene glycol derivatives, or polyethylene glycol-thiol.

Cytokine constructs of the disclosure comprising Tumor Necrosis Factor alpha (TNFα) and Interferon gamma (IFNγ) may further comprise paclitaxel, paclitaxel analogue or paclitaxel prodrug.

In an embodiment, provided herein are methods for increasing cytokine cytotoxicity, comprising the steps of combining a gold nanoparticle with two types of cytokines to create a construct, wherein the cytokines consist of Tumor Necrosis Factor alpha (TNFα) and IFN gamma (IFNγ), introducing the construct to a biological sample containing cells and assessing the cytotoxicity of the construct on the cells, wherein the cytotoxicity is increased compared to introduction of (a) native cytokines and/or (b) an individual cytokine bound to a gold nanoparticle. Such methods may be carried out on biological samples comprising cancer cells, and more specifically on thyroid cancer cells. Cytotoxicity may be measured using a cell viability assay.

In an embodiment, provided herein are methods for increasing cytokine potency, comprising the steps of combining a gold nanoparticle with two types of cytokines to create a construct, wherein the cytokines consist of Tumor Necrosis Factor alpha (TNFα) and Interleukin-12 (IL-12), introducing the construct to a biological sample containing cells and assessing the potency of the construct on the cells, wherein potency is increased compared to introduction of native cytokines. Potency may be measured using a HEK bioassay for assessing receptor activation. HEK bioassays, as used herein, are HEK cell-based functional assays to study receptor activity through a fluorescent output.

In an embodiment, provided herein are methods for inducing MHC-1 (13) expression in cancer cells, comprising introducing a cytokine construct to cancer cells, wherein the cytokine construct comprises Tumor Necrosis Factor alpha (TNFα) and IFN gamma (IFNγ) bound to a gold nanoparticle. Cancer cells may comprise lung cancer cells or thyroid cancer cells.

In an embodiment, provided herein are methods for activating naïve lymphocytes in a biological sample containing cancer cells comprising introducing a cytokine construct to the biological sample to induce MHC-1 (HLA-A-C) expression, followed by the addition of lymphocytes; wherein the cytokine construct consists of Tumor Necrosis Factor alpha (TNFα) and IFN gamma (IFNγ) bound to a gold nanoparticle, wherein the cytokine construct has a cytotoxic effect on the cancer cells and an activating effect on the lymphocytes.

In an embodiment, provided herein are methods for treating cancer in a subject in need thereof, comprising administering a cytokine construct to the subject, wherein the cytokine construct comprises Tumor Necrosis Factor alpha (TNFα) and IFN gamma (IFNγ) bound to a gold nanoparticle. In such an embodiment, the construct may further comprise polyethylene glycol, polyethylene glycol derivatives, or polyethylene glycol-thiol and the ratio of TNFα to IFNγ is about 20:1 (w/w). In such an embodiment, the construct may further comprise paclitaxel, or a paclitaxel analogue or prodrug.

Provided herein are compositions and methods related to constructs comprising colloidal gold nanoparticles and cytokines, optionally combined with one or more therapeutic agents, and optionally polyethylene glycol molecules. The types of cytokines consist of Tumor Necrosis Factor alpha (TNFα), and interferon gamma (IFNγ) or Interleukin-12 (IL-12) or Interleukin-2 (IL-2). The polyethylene glycol molecules may comprise a polyethylene glycol derivative covalently bound to the colloidal gold nanoparticle.

In an embodiment of the invention, methods for treating diseases and disorders comprising the administration of a cytokine construct is provided. In such an embodiment, methods for treating a solid tumor, comprise administering a composition to an organism having the solid tumor, wherein the composition comprises cytokine constructs consisting of colloidal gold particles and two types of cytokines, optionally combined with one or more therapeutic agents, one or more polyethylene glycol molecules; wherein the colloidal gold particles consist of gold nanoparticles and wherein the two types of cytokines bound to the gold nanoparticles consist of TNFα and IFNγ.

In certain embodiments, the cancer is melanoma. In certain embodiments, the cancer is a solid tumor. In certain embodiments, methods for treating solid tumors comprise the administration of novel cytokine construct compositions to an organism having a solid tumor, wherein the novel cytokine constructs comprise a gold nanoparticle bound to two types of cytokines, wherein the two types of cytokines comprise Tumor Necrosis Factor alpha (TNFα) and Interferon gamma (IFNγ).

The following examples are given to illustrate exemplary embodiments of the present disclosure. It should be understood, however, that the present disclosure is not to be limited to the specific conditions or details described in these examples. Examples are provided below to facilitate a more complete understanding of the invention. The following examples illustrate the exemplary modes of making and practicing the invention.

EXAMPLES

Background

Manufacturing CYT-IFNγ-TNFα

Two methods were used to produce CYT-IFNγ-TNFα. The first involves the simultaneous binding of TNFα, IFNγ and PEG-THIOL to the surface of the gold nanoparticles. The second involves the sequential binding of TNFα followed by the simultaneous binding of IFNγ and PEG-THIOL.

For these studies, the pH of the colloidal gold solution was adjusted to approximately 8.0 by the stepwise addition of a 50 mM solution of sodium borate (NaBo). Similarly, the binding buffer (BB), the solution used to dilute TNFα (CytImmune Sciences, Inc.), IFNγ (R&D Systems) and 20 kDa form of PEG-THIOL (SunBio, Inc.) was similarly adjusted to 8.0 with NaBo. TNFα, IFNγ and PEG-THIOL were diluted into the BB to final concentrations of 0.25, 5.0 and 15 μg/mL, respectively. Equal volumes of both the gold nanoparticles and BB (containing the various reagents) were combined, by the rapid addition of the BB solution to the gold nanoparticle solution, under a strong vortex. The solutions were incubated for a minimum of 3 hours.

Subsequently, particle-bound vs free reagents were separated by centrifugation, although one skilled in the art could easily employ ultrafiltration with an appropriate apparatus, such as a UF cartridge or hollow fiber assembly. The concentrated nanoparticles were washed two times using an isotonic solution and upon the final concentration step, the gold nanoparticles were aliquoted and frozen at −80° C. Alternatively, a lyophilization cycle for the long-term storage of the nanodrugs at −20° to +4° C. may be used.

Measurement of Bound Vs Free TNFα and IFNγ

Cytokine-specific sandwich ELISAs were used to measure both the particle-bound and free fractions of TNFα and IFNγ. Both ELISAs use commercially available cytokine-specific neutralizing monoclonal antibodies (R&D Systems) to capture either TNFα or IFNγ bound to the particles or free in solution. Once captured, cytokine-specific rabbit polyclonal antibodies (CytImmune Sciences, Inc.) were added to the wells and the complex was detected with alkaline phosphatase conjugated goat-anti-rabbit antibodies (Sigma). The concentration of each cytokine was determined by regression analysis against known standards. Depending on the scale TNFα and IFNγ concentrations typically ranged from 2 to 40 μg/mL, respectively, with 90-95% of the cytokine measured as being bound to the gold nanoparticles.

Example 1

Cross Antibody ELISA: A Qualitative Demonstration that Both IFNγ and TNFα are on the Same Gold Nanoparticle Although the ELISAs described in Example 1 are useful to quantitate the relative amounts of both IFNγ and TNFα on the particle surface they do not demonstrate the presence of both cytokines on the same particle.

Figure 2A:
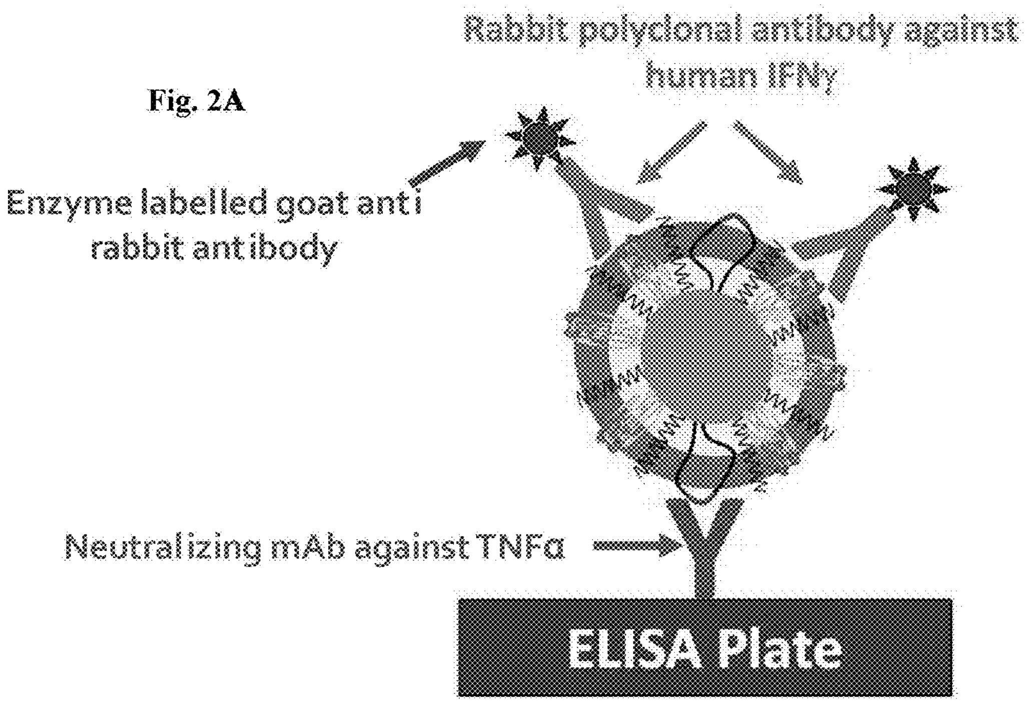
FIGS. 2A-2B provide a schematic of the cross-antibody ELISA (FIG. 2A), and results of the cross-antibody ELISA using the method (FIG. 2B). For this assay a TNFα-only nanoparticle was used as a control. Both the experimental CYT-IFNγ-TNFα nanoparticle and control were captured by the TNFα mAb, however, because the control lacks IFNγ it did not generate a signal in the ELISA. Preparations containing IFNγ generated a significant signal whose amplitude was dependent on the amount of IFNγ added during binding.

To address this need, a cross-antibody (XAb) ELISA was developed (FIG. 2A) in which the nanoparticle is captured by a monoclonal antibody specific to a first cytokine and detected with the polyclonal (rabbit) antibody against the second cytokine.

Figure 2B:
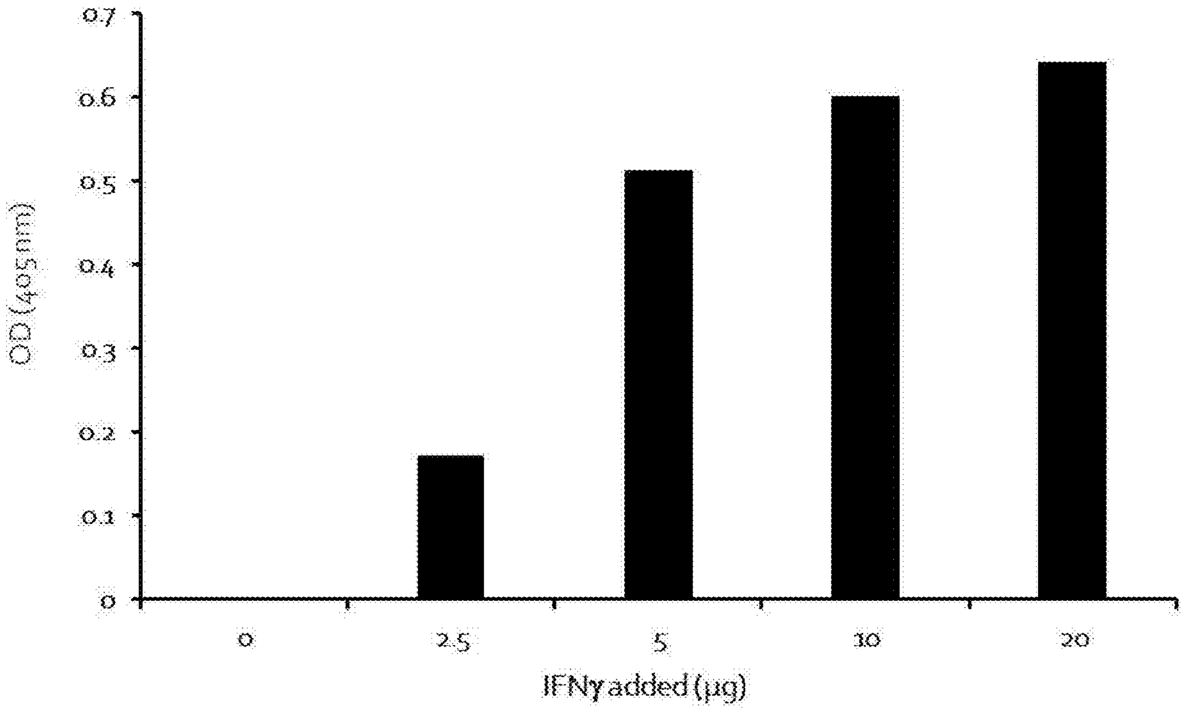

In one version of the XAb ELISA we used the murine monoclonal antibody against TNFα to capture the CYT-IFNγ-TNFα or the single-agent controls which were bound solely with TNFα. Once the nanoparticles were captured by the mAb (following and incubation at RT for 4-24H), the plates were washed and the rabbit polyclonal antibody against human IFNγ was used as the detection system. As shown in FIG. 2B the single agent TNFα nanoparticles generated little to no signal in the XAb ELISA. Not only did CYT-IFNγ-TNFα generate a significant signal in the XAb ELISA, but the amount of color that was developed was dependent on the amount of IFNγ bound initially bound to the nanoparticles during manufacturing.

Binding, Uptake and Internalization of CYT-IFNγ-TNFα by the Follicular Thyroid Cancer Cell Line, FTC-133

For these studies 5,000-10,000 FTC-133 cells were plated in 6-well tissue culture clusters in 2 mL of complete DMEM. The cells were maintained under standard tissue culture conditions (37° C., 95% relative humidity). 24-48 hours later, CYT-IFNγ-TNFα (between 0.05-2.0 μg of IFNγ) was added to the media and the uptake of the nanoparticle by the cells was imaged under bright field or phase contrast microscopy at various times after the addition of the nanoparticle.

Figure 3A:
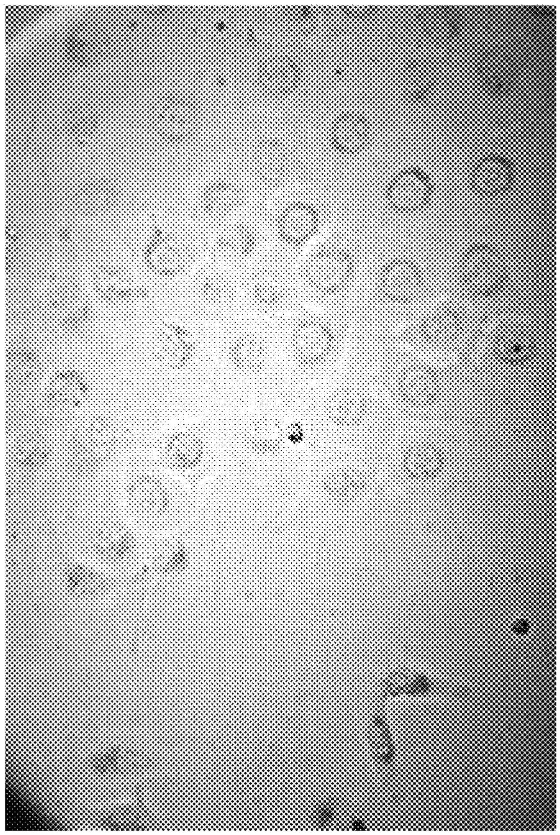
FIGS. 3A-3C provide micrographs showing the binding and internalization of CYT-IFNγ-TNFα by the Follicular Thyroid cancer cell line, FTC-133 (4). CYT-IFNγ-TNFα was added to FTC-133 cells and its binding and internalization was observed by bright field microscopy.
Figure 3B:
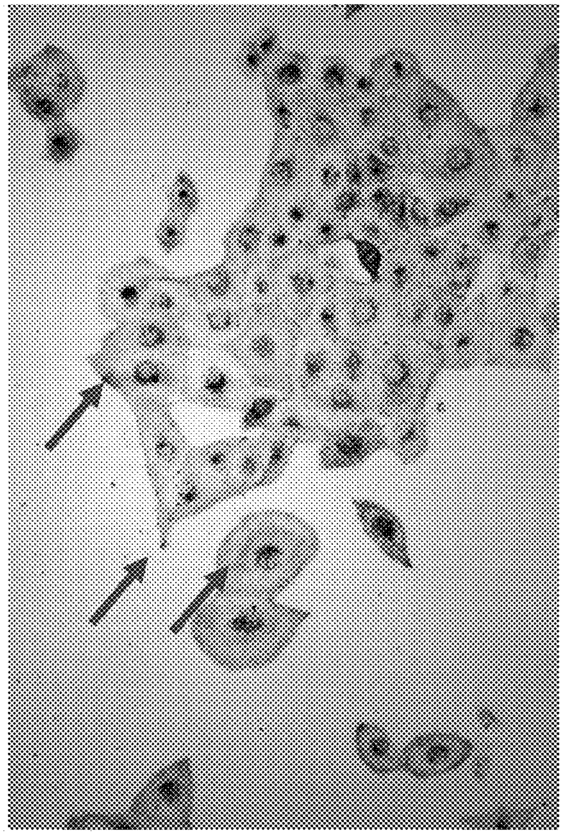
Figure 3C:
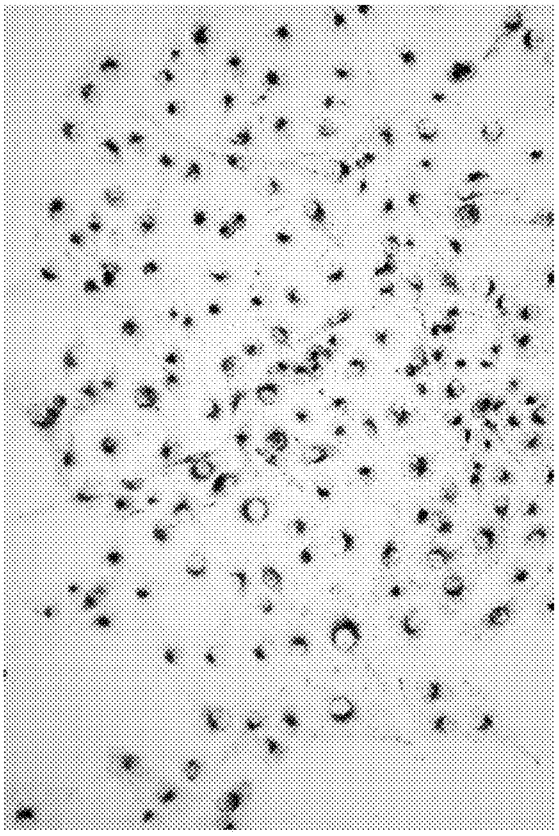
Figure 4A:
FIGS. 4A-4D provide micrographs showing cytokine-based-nanoparticle-induced cytotoxicity in FTC-133 cells. FTC-133 cells were plated in 6-well tissue culture clusters in complete DMEM. 24-48 hours after plating (to allow the cells to adhere) various nanoparticles were added to the cells at 1 μg/mL. Nanoparticle treatments are depicted as follows: No treatment (FIG. 4A); CYT-6091 (TNFα single agent.
Figure 4B:
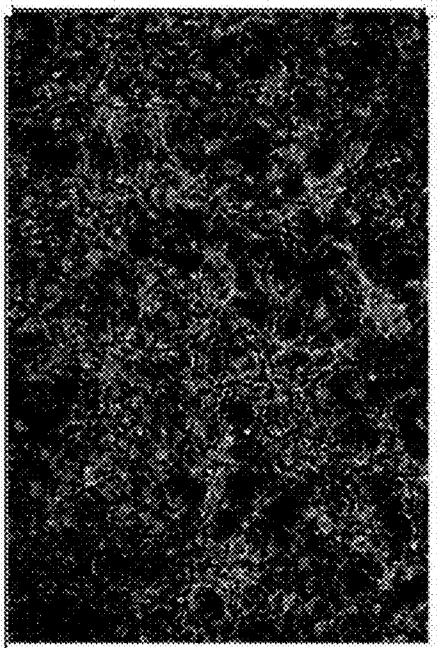
Figure 4C:
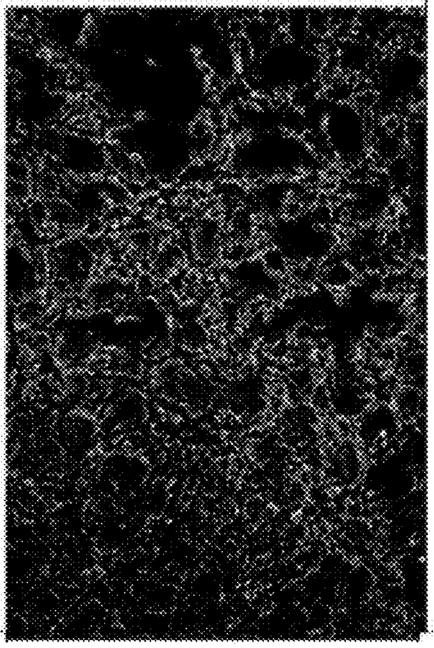
Figure 4D:
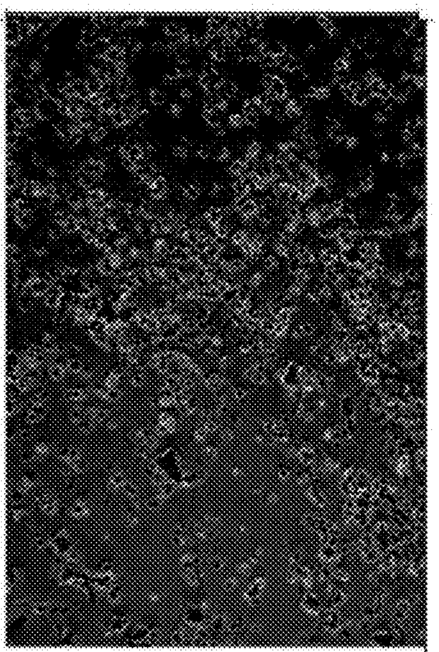

As shown in FIG. 3, the uptake of CYT-IFNγ-TNFα by FTC-133 cells was observed as the cells acquired the reddish color of the colloidal gold nanoparticles. Within 15-45 minutes of addition of the nanoparticle, the particles were evenly distributed over the surface of the cell. Over the next 90 minutes the pattern of staining was localized in distinct areas of the cell (see example discussing receptor clustering below). Finally, eight to twelve hours later the particles were visualized as black aggregates in a perinuclear region of the cell.

Assessment of Cytotoxicity

Given the uptake of the nanoparticle and the fact that both TNFα and IFNγ are known to induce cytotoxicity in certain cancer cell lines the experiments were repeated but the growth of the cells was determined after an additional incubation period of 5-7 days. Additionally, additional nanoparticles, such as CYT-6091 (see below) and the single-agent interferon gamma nanoparticle were also included.

Shown in FIG. 4 are the photomicrographs of the various cultures described above. The data in FIG. 4 demonstrate that both CYT-6091 and CYT-IFNγ were cytotoxic to FTC-133 cells since the wells were less confluent vs the untreated controls (FIG. 4A). However, CYT-IFNγ-TNFα exhibited the greatest degree of cytotoxicity as no viable cells could be identified in the cultures.

Example 2

CYT-IFNγ-TNFα Increases the Potency of IFNγ and TNFα

In this study we compared the potency of CYT-IFNγ-TNFα vs the same dose of IFNγ and TNFα in solution. Small scale batches of the nanoparticle were produced as described above and the concentration of the particle bound cytokines was determined by quantitative ELISA. Subsequently, increasing concentrations of IFNγ and TNFα, added as CYT-IFNγ-TNFα, were added to FTC-133 cells growing in 96 well tissue culture clusters. In another group of wells, the same doses of native IFNγ and TNFα were added at the same concentration as CYT-IFNγ-TNFα. The native cytokines were added as a single solution.

The cells were incubated for an additional 2-3 days at 37° C. and at 95% relative humidity. Subsequently, the incubation media was removed, and the cells were gently washed 3 times in serum free DMEM. After the final wash, 100 μL of complete DMEM was added back to the cells followed by the addition of 10 μL of Alamar Blue™. The plates were incubated at 37° C. until the fluorescence for untreated/control wells obtained a value of $10^4$ relative fluorescence units.

Figure 5A:
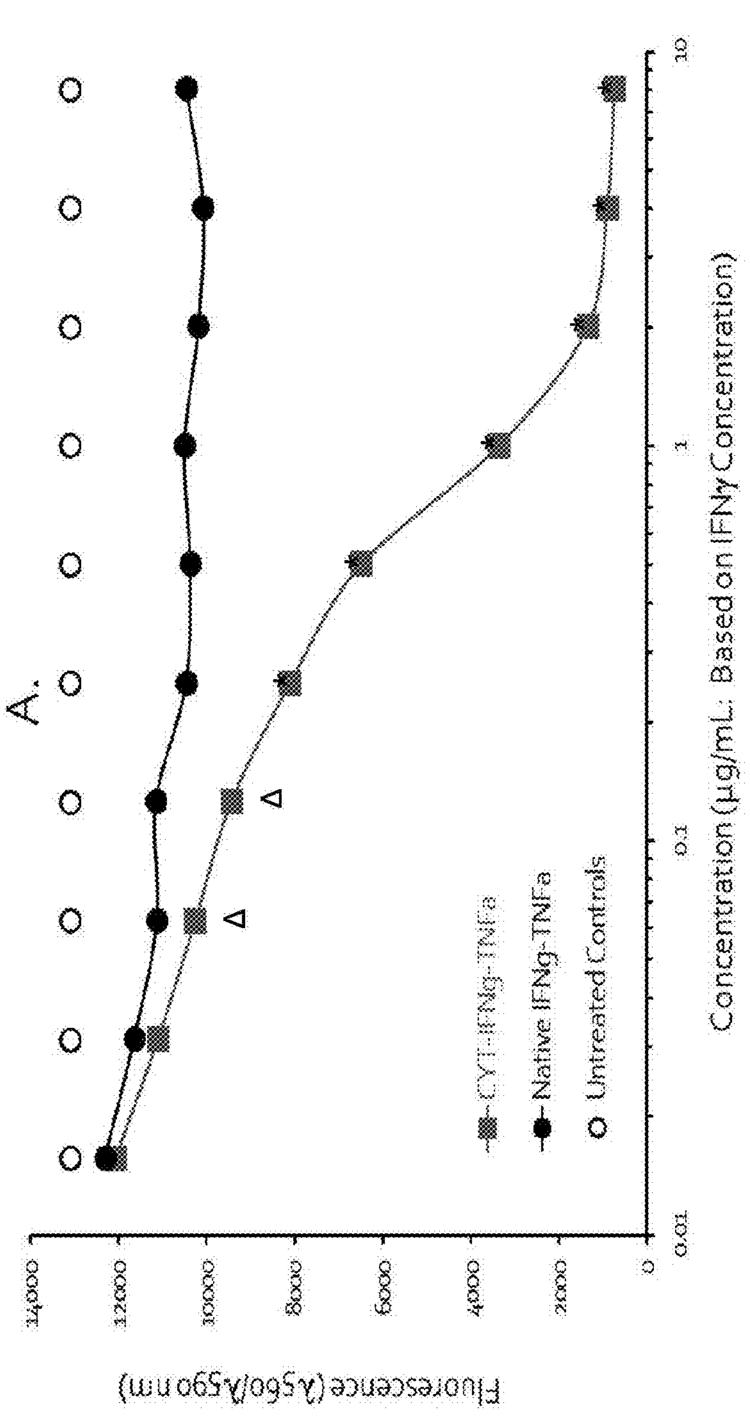
FIG. 5A and FIG. 5B provide graphs showing that CYT-IFNγ-TNFα is more cytotoxic to FTC-133Cells (FIG. 5A) versus the same doses of the native cytokines TNFα (FIG. 5B) and IFNγ (FIG. 5C) in solution. The data presented are from two separate experiments with quadruplicate well per concentration. The data clearly show that native IFNγ-TNFα were marginally cytotoxic to the FTC-133 cells when compared to the same doses of the cytokine added as CYT-IFNγ-TNFα. A similar pattern was observed with single agent nanoparticles: CYT-IFNγ-TNFα exhibited greater potency vs CYT-6091 (the single agent TNFα nanoparticle or CYT-IFNγ (the single agent IFNγ nanoparticle).
Figure 5B:
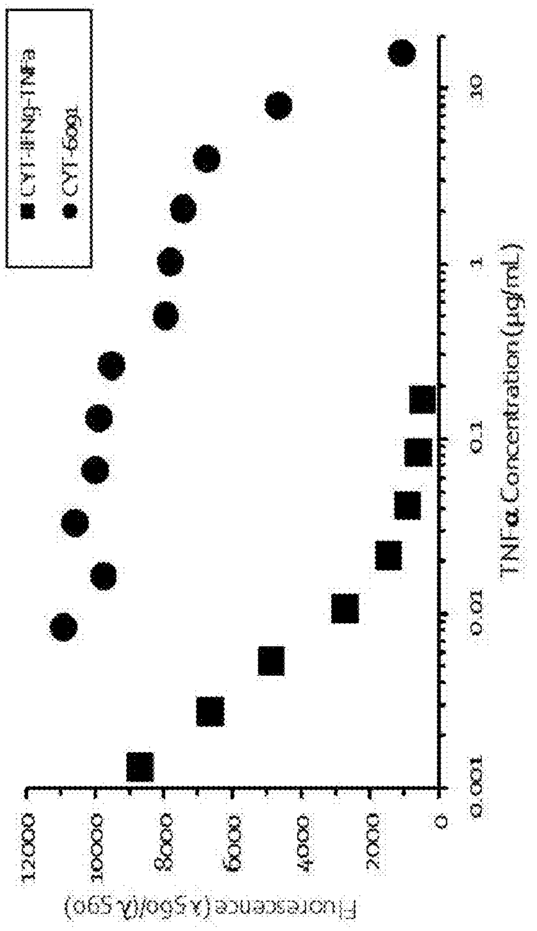
Figure 5C:
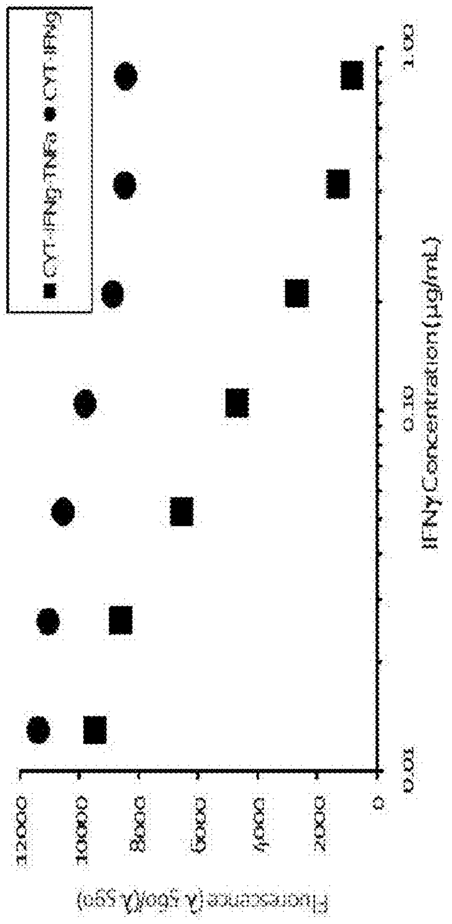

As shown in FIG. 5 CYT-IFNγ-TNFα increased the dose-to-dose cytotoxicity of IFNγ/TNFα in the FTC-133 cells. These data are consistent with a more efficient interaction of IFNγ/TNFα with their respective receptors, possibly by inducing receptor clustering (see below).

CYT-IFNγ-TNFα Increases the Potency of IFNγ TNFα in a Genetically Engineered Cell Line HEK-IFNγ (InvivoGen, California, USA) is an engineered HEK cell line which has been stably transfected with the IFNγ receptor/signaling machinery. In this cell line, the binding of IFNγ to its receptor induces expression and secretion of an alkaline phosphatase reporter gene. The amount of alkaline phosphatase produced is directly proportional to the amount of IFNγ present in the sample. The amount of the reporter gene that is released can be assayed by adding tissue culture supernatants to fixed volumes of the PNPP (p-Nitrophenyl Phosphate; Sigma Aldrich, Missouri, USA) substrate.

Figure 6:
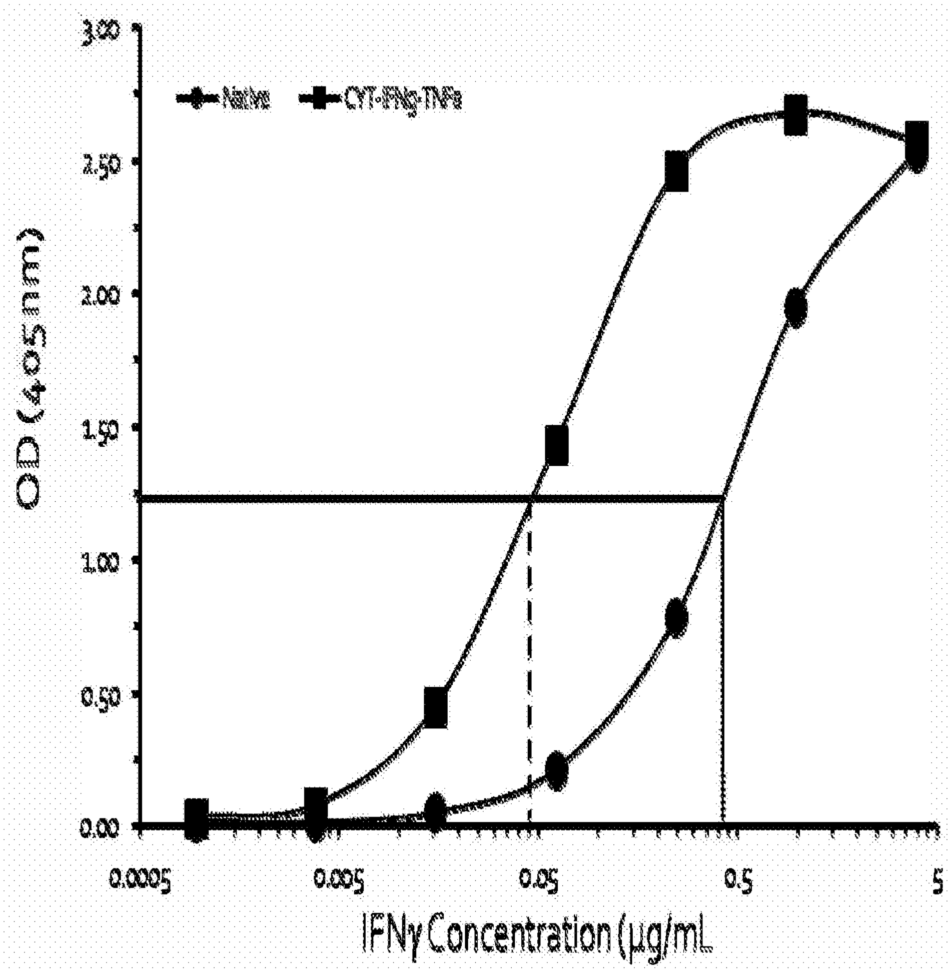
FIG. 6 provides a graph showing that CYT-IFNγ-TNFα exhibits similar increases in potency as compared to native IFNγ in a genetically engineered cell line, HEK-IFNγ. HEK cells were stably transfected with the IFNγ receptor and signaling complexes. Potency is based on IFNγ concentrations (FIG. 6).

To evaluate whether CYT-IFNγ-TNFα induced similar increases in potency, as demonstrated in cytotoxicity studies, these cells were used in similar studies as described in FIGS. 5A and 6. Briefly, 20,000 HEK-IFNγ cells were plated as outlined by the manufacturer. The following day increasing concentrations of IFNγ and TNFα were added in a single solution or as CYT-IFNγ-TNFα. The cells were incubated for an additional 48 hours. Afterwards, 10 μL of the tissue culture supernatant were collected and added to 200 μL of the PNPP substrate. The reaction was monitored by measuring the OD at 405 nm and terminated when the Optical Density for the highest dose obtained OD between 2.0-3.0 OD units.

The combination of native IFNγ/TNFα induced dose dependent increases in the relative amounts of the alkaline phosphatase secreted by the HEK-INFg cells. Unlike the FTC-133, wherein the native cytokine combination exhibited marginal activity, the HEK-IFNγ data are anticipated as the cells are engineered to secrete the reporter protein in a dose dependent manner. However, the data presented in FIG. 6 are consistent with those reported in FIG. 5 as a similar increase in potency (15-fold decrease in the $EC_{50}$) was observed in the cells receiving CYT-IFNγ-TNFα.

Cytokine Stability Afforded by the Gold Nanoparticles

The increase in potency observed in CYT-IFNγ-TNFα may in part be due to mechanisms by which the gold nanoparticles improve the stability of the cytokine. To test this in a simple matrix, equal concentrations of both native IFNγ and TNF or CYT-IFNγ-TNFα were added to FTC-133 cells which were subsequently cultured at 37° C. for 2 days. On the second day aliquots of each set of samples were collected, frozen at −80° C. and analyzed by ELISA.

Figure 7:
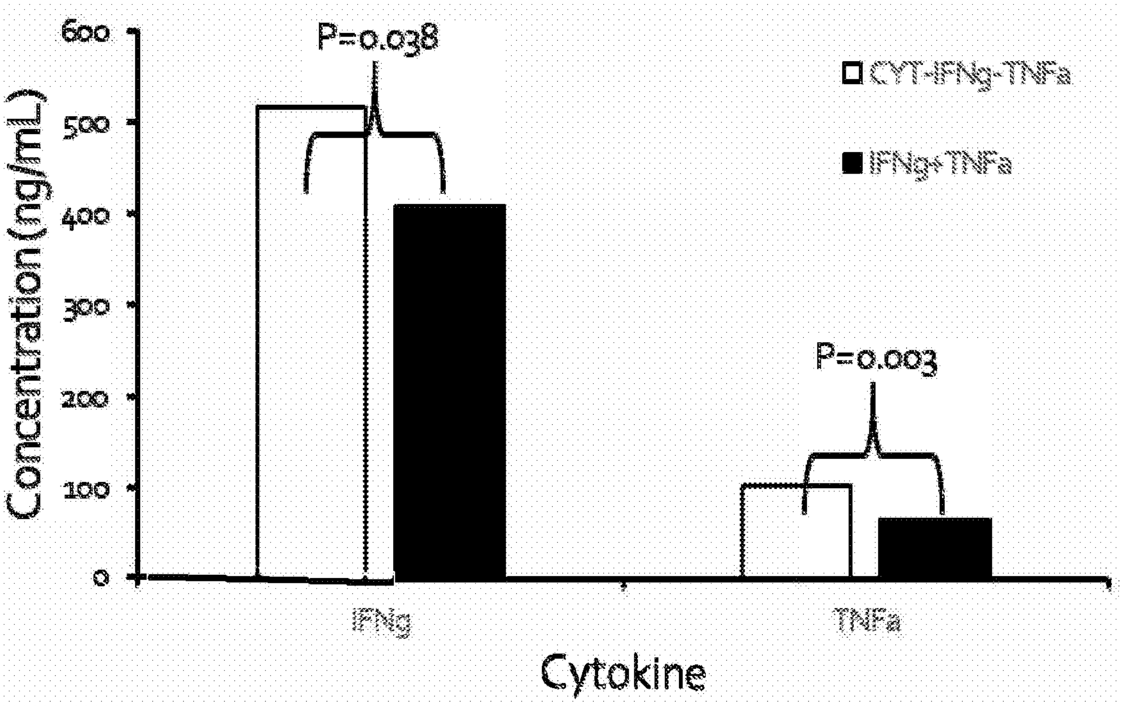
FIG. 7 provides a graph showing the slight increase in cytokine stability is not the mechanism underlying the increase in potency observed in the CYT-IFNγ-TNFα preparations (see FIGS. 4 and 5 for detail).

The data shown in FIG. 7 illustrate that a minor, approximately 20%, decrease in recovered cytokine concentration was measured in the native cytokine samples. While significant, it is unlikely that the decrease could explain the differences in potency between the two preparations. It is noted however, that increasing cytokine stability afforded by binding the cytokines to the particle surface is desirable.

Evidence of Receptor Clustering

Though not wishing to be bound by the following theory, it is hypothesized that the increased potency reported in FIG. 5 may be mediated by receptor clustering. Given that both IFNγ and TNFα are biologically active on the particle surface (the quantitative ELISA utilizes neutralizing mAbs specific for each cytokine to capture CYT-IFNγ-TNFα), it was hypothesized that when presented on the particle surface, IFNγ and possibly TNFα induce an avidity event for their respective receptor. Given these observations, the gold nanoparticle platform was used to generate initial evidence supporting receptor clustering.

To test this hypothesis, the imaging studies outlined in Example 1 were repeated with the cells imaged between 90 minutes and 8 hours following the addition of CYT-IFNγ-TNFα. The cells were imaged by both bright field and phase contrast microscopy to identify the trafficking of the nanoparticles.

Figure 8:
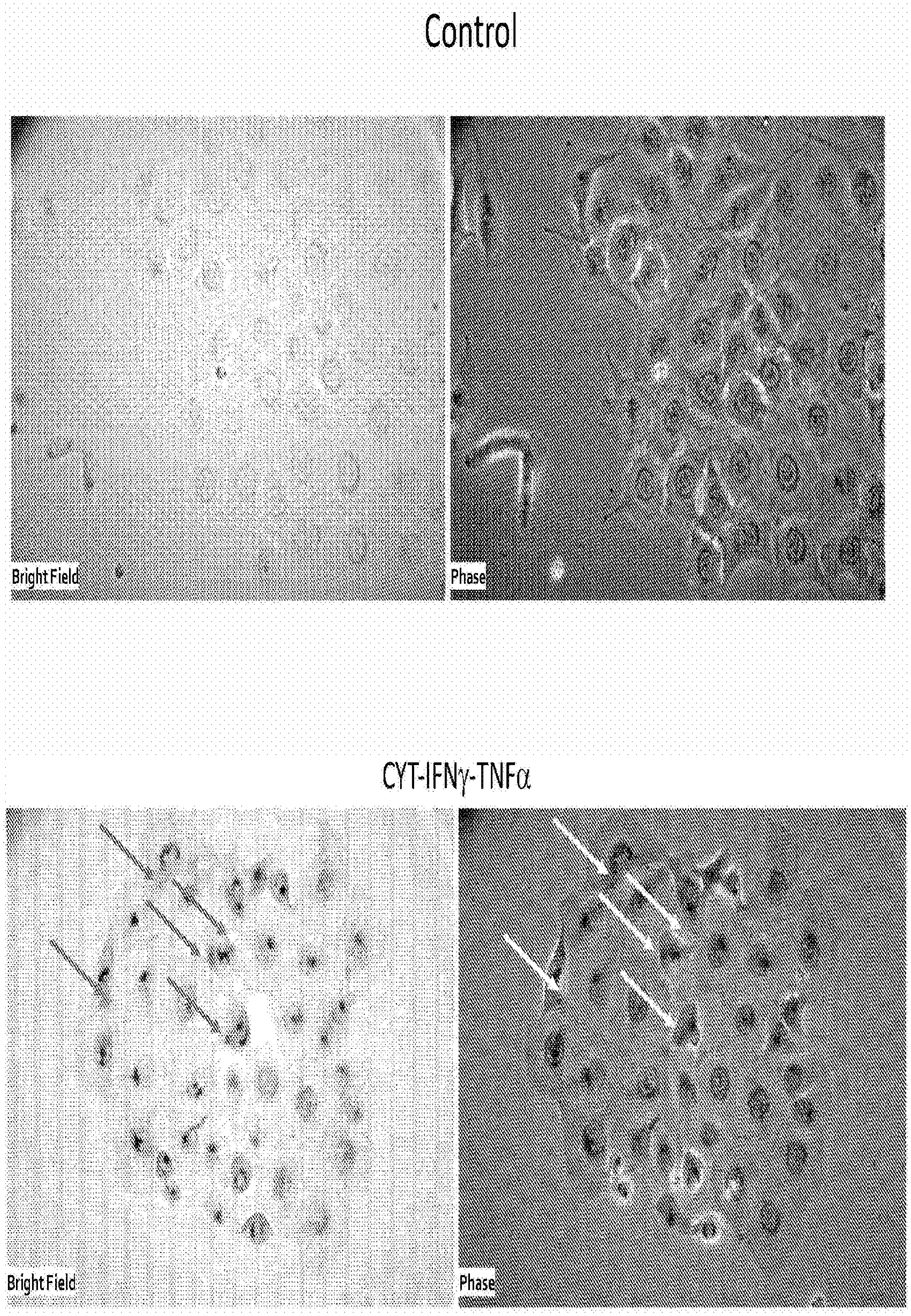
FIG. 8 provides micrographs showing that CYT-IFNγ-TNFα induces receptor clustering. Control (no treatment) or CYT-IFNγ-TNFα treated FTC-133 cells were imaged 3 hours post addition of CYT-IFNγ-TNFα. The images illustrate the different stages of nanoparticle uptake by FTC-133 cells.
Figures 9A, 9B, 9C:
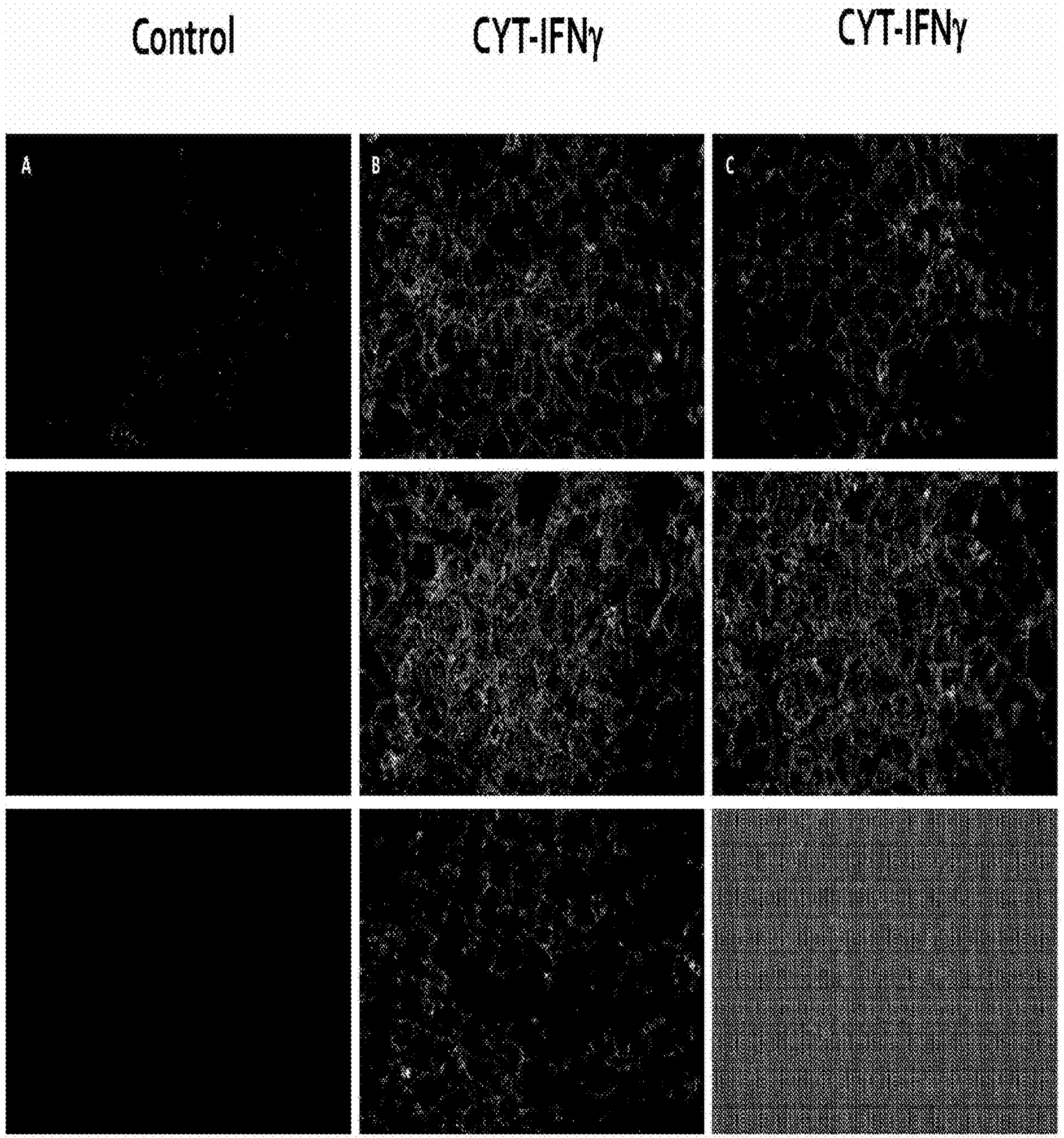
Figures 9D, 9E, 9F, 9G:
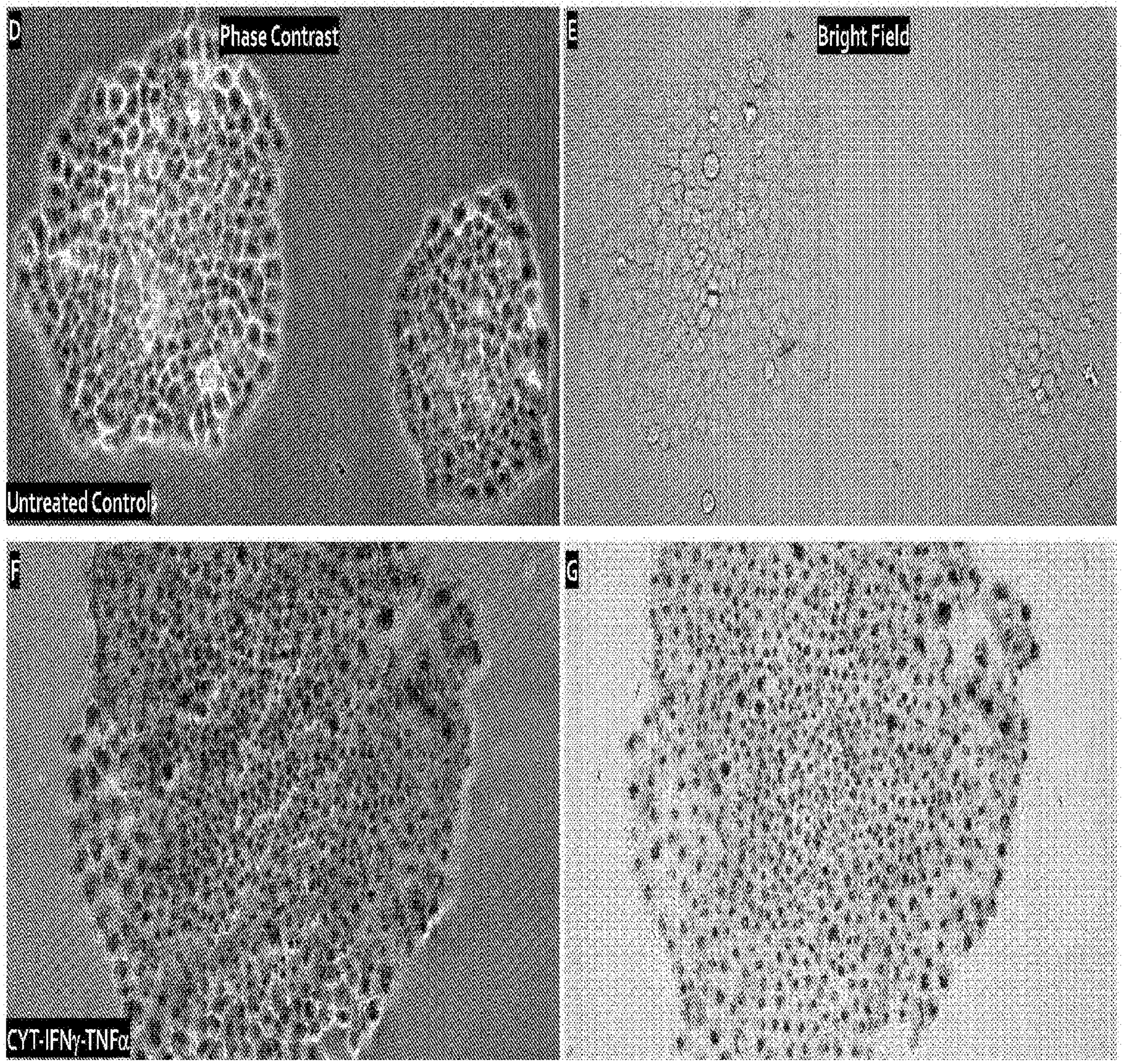
FIGS. 9D-9G illustrate the uptake and internalization of CYT-IFNγ-TNFα by the human lung cancer cell line H-460. The pattern of uptake is similar to that of the FTC-133 cells shown in FIG. 3.
Figures 9H, 9I, 9J, 9K:
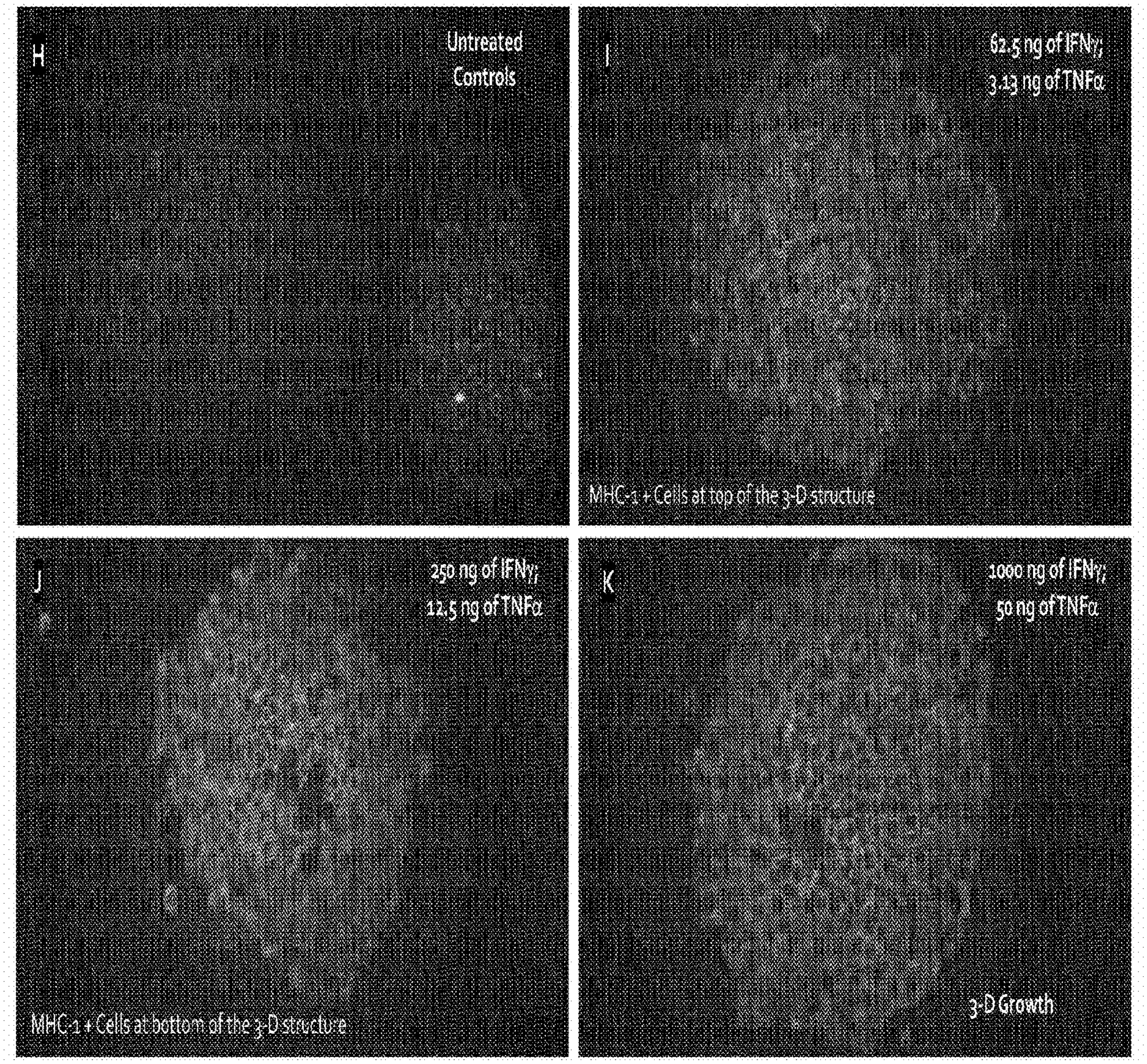
FIGS. 9H-9K show that, similar to FTC-133 cells, CYT-IFNγ-TNFα induced the expression of HLA-A-C throughout the three-dimensional cluster typically formed by H460 cells.
Figures 9L, 9M, 9N, 9O:
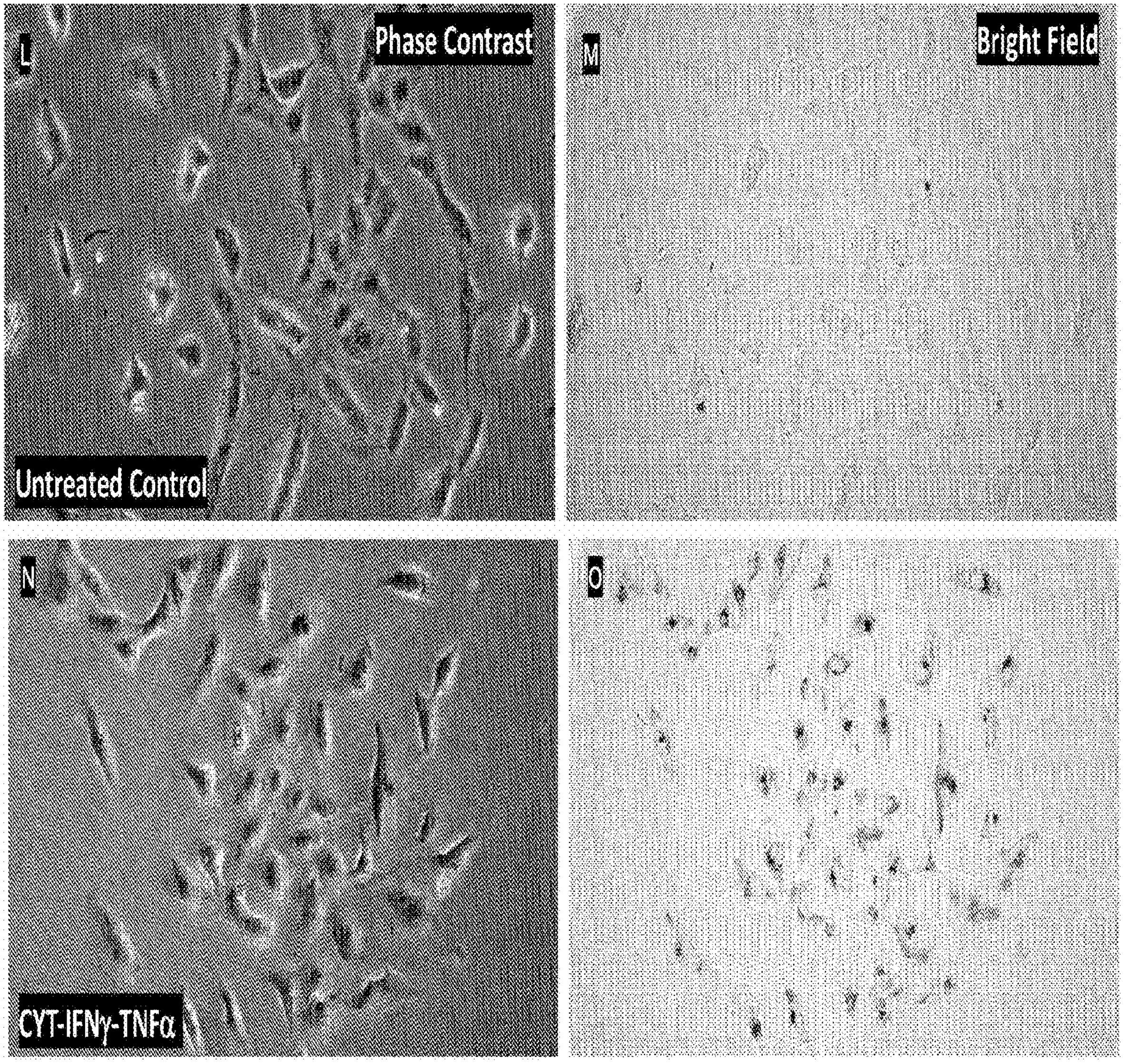
Figures 9P, 9Q, 9R, 9S:
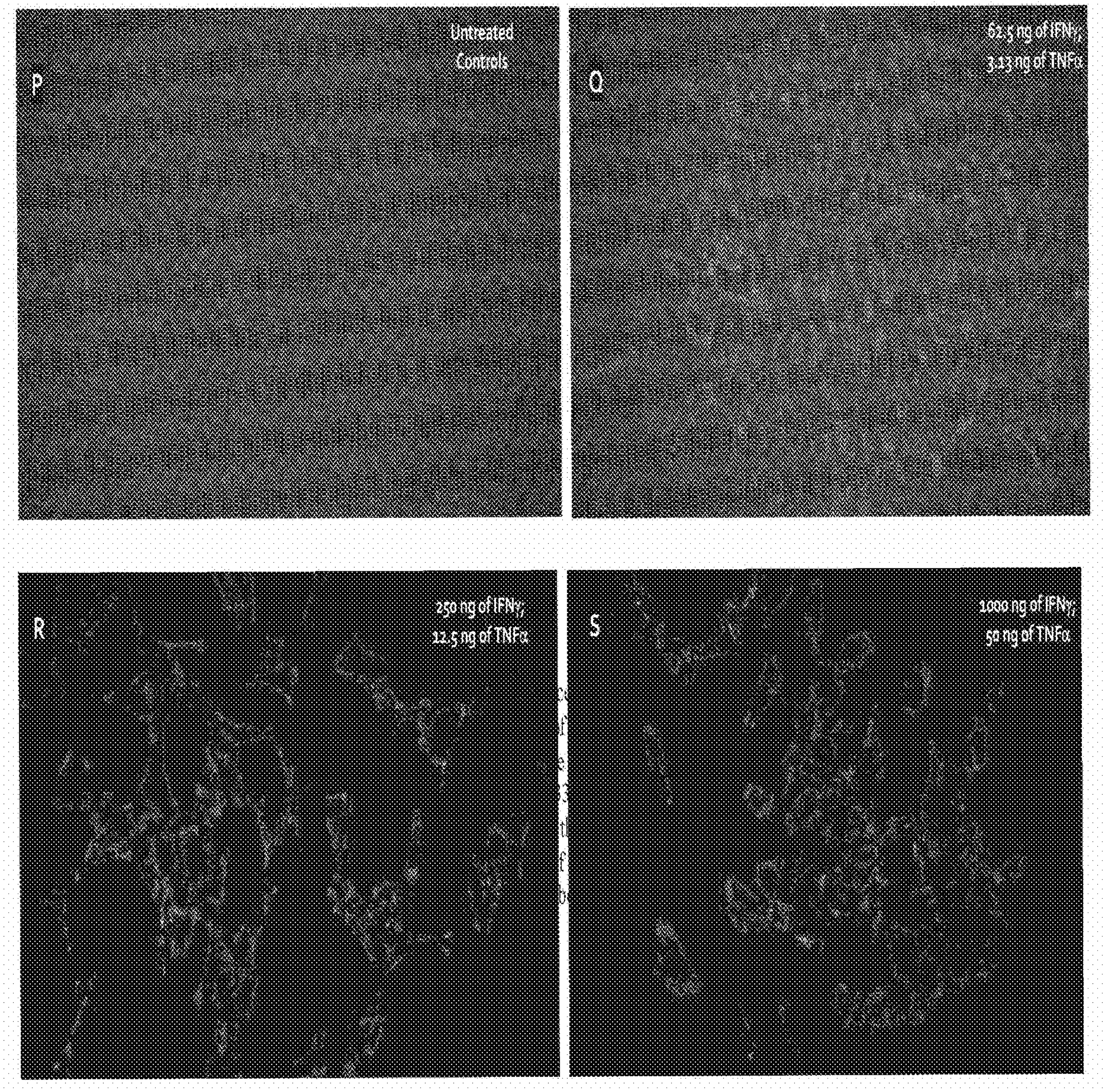

The data presented in FIG. 8 are consistent with receptor clustering and internalization of the particles presumably within endosomes. Within the endosome, the particle bound constituents (TNFα, IFNγ and PEG-THIOL) were either degraded or released from the particle surface, and lacking any passivating agent, these so-called "naked particles" aggregated as they migrated toward the nucleus.

Unlike the near transparent image of control FTC-133 cells (top left panel), many of the cells exhibit a pink color highlighting the presence of the nanoparticle on the cell surface. Similarly, all of the CYT-IFNγ-TNFα treated FTC-133 cells exhibited perinuclear localization of the particles, evidenced as black precipitates around the nucleus. Additionally, in several cells, highlighted by the arrows in the bright field (bottom left panel) and the phase contrast images (bottom right panel), the pattern of nanoparticle uptake was punctate in nature. While mechanism of action studies are not presented, these initial data support that CYT-IFNγ-TNFα induced clustering of their target receptor.

Example 3

Induction of MHC-1 by CYT-IFNγ-TNFα

Many tumors escape detection and elimination by the immune system by either poorly or not expressing the major histocompatibility antigen (13-14). In humans, this complex has been designated HLA A-C with the murine equivalent termed MHC-1. IFNγ is known to upregulate MHC-1 expression (12). To test this hypothesis, we evaluated both baseline (untreated) and CYT-IFNγ-TNFα-induced expression of the histocompatibility complexes in both human and murine cancer cells lines.

For these studies numerous cell lines including FTC-133 (human thyroid cancer), H460 and A549 (human lung cancer), Colo26 (murine colon carcinoma isolated from Balb C mice) and B16F10 (melanoma cell line isolated in C57Bl/6 mice) were used. Approximately 20,000 cells for each cell line were plated in 6-well tissue culture plates and incubated under standard culture conditions for 48 hours. Subsequently the cells were incubated with either the human nanoparticle CYT-IFNγ-TNFα or the murine equivalent, CYT-mIFNγ-hTNFα.

Generating a murine nanoparticle was required since, unlike human TNFα, human IFNγ is not cross-reactive in mice. This variant was produced and interrogated by the methods outlined in the above examples.

For these studies, between 0.0625 to 1 μg of the CYT-IFNγ-TNFα (the human nanoparticle) or CYT-mIFNγ-TNFα (the murine nanoparticle) were incubated with FTC-133, H460, and A549 cells or Colo 26 or B16F10 cancer cells, respectively. 48 hours later, the cells were washed 2 times with incomplete DMEM and 1 μg of a mouse monoclonal antibody (Sigma Aldridge) that recognizes both the HLA-A-C and the murine MHC-1 complexes was added to the cultures. The antibody was diluted in complete DMEM and incubated with the cells for 1 hour. Subsequently, the cells were once again washed 2 times with incomplete DMEM, and a FITC-conjugated goat anti-mouse polyclonal antibody (Sigma Aldrich) was added to the cultures. The antibody was incubated for an additional hour. The cells were washed one final time with incomplete DMEM, and the presence of the HLA-A-C or MHC-1 complex was documented by fluorescent microscopy.

Shown in FIG. 9 are confirmatory data that CYT-IFNγ-TNFα induced HLA-expression in the FTC-133, HL-460 and A549 human cancer cell lines (See FIGS. 9A-9C, 9D-9K, and FIGS. 9L-9O, respectively). The induction of HLA A-C (FIGS. 9P-S) in both H460 and A549 occurred over a wide dose range. Consistent with the hypothesis presented by Angell et. al., (12) control cells exhibited no or marginal expression of the HLA-A-C complex whereas cultures treated with the nanoparticle exhibited significant staining for the antigen.

Furthermore, both human lung cancer cell lines exhibited similar pattern of CYT-IFNγ-TNFα uptake as evidenced by the pink/black staining of the cells to highlighting binding and internalization of the nanoparticle and subsequent expression of HLA-complex (FIGS. 9D-9G for the H-460 cancer cell line and FIGS. 9L-9O for the A549 cancer cell line).

Generation of an Anti-Cancer Immune Response by CYT-mIFNγ-TNFα

In the following study we determined whether the induction of MHC-1 by CYT-IFNγ-TNFα would lead to a de novo anti-cancer immune response. For this study either Colo 26 or B16F10 cancer cells were plated and treated with the murine variant of CYT-IFNγ-TNFα (CYT-mIFNγ-hTNFα) as described above. Controls were cancer cells receiving no treatment. After MHC-1 induction was confirmed, approximately $10^6$ splenocytes from naïve Balb/c were added to the Colo 26 cultures. A similar number of splenocytes harvested from C57Bl/6 mice were added to either control or nanoparticle treated cultures and the induction of an anti-cancer immune response was confirmed by the proliferation of the splenocytes.

Figures 10A, 10B:
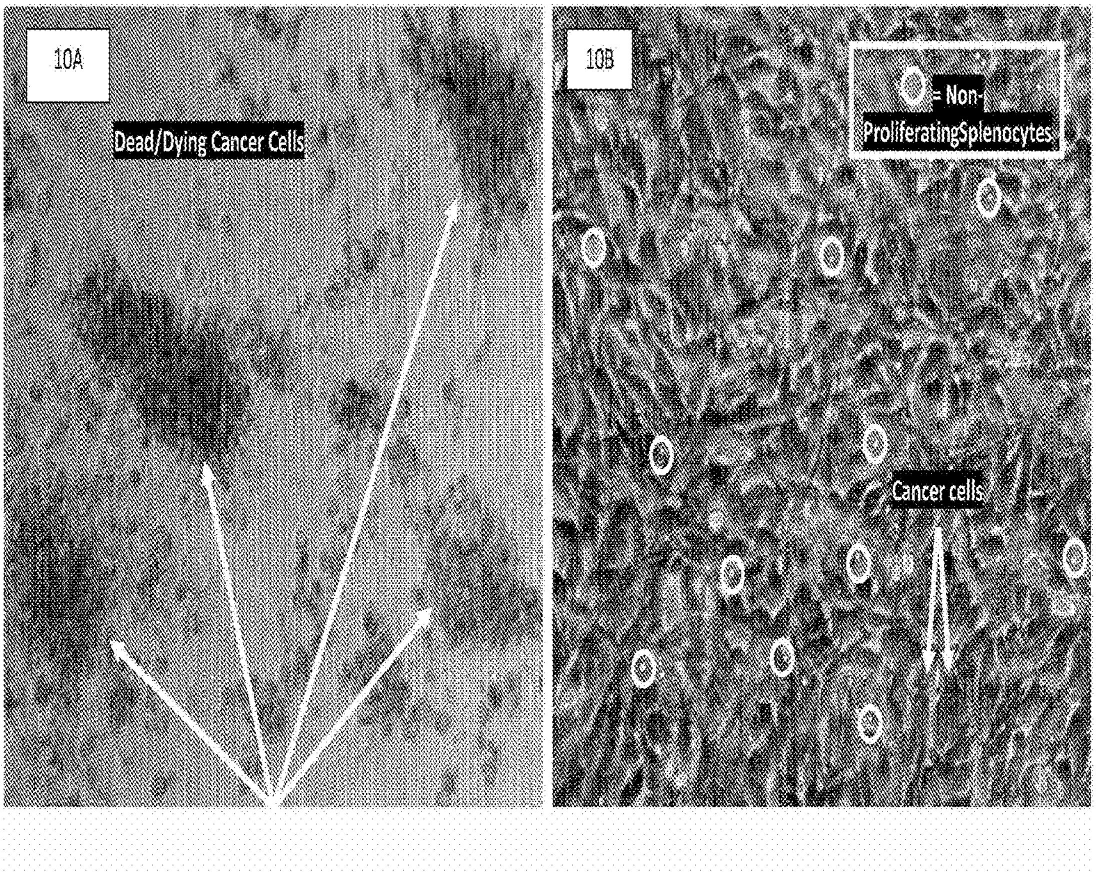

The data presented in FIG. 10 support that CYT-mIFNγ-hTNFα induced splenocytes harvested from naïve Balb/c mice to proliferate. Several observations were noted in these cultures. Consistent with the data shown in FIGS. 4-5, CYT-mIFNγ-TNFα induced profound inhibition of Colo26 cell proliferation (FIG. 10A) when compared to untreated controls (FIG. 10B). Further, the nanoparticle activated naïve splenocytes to proliferate directly on the surface of the remaining cancer cells. These data are consistent with nanoparticle-induced proliferation of naïve B-cells reported by Paciotti et al., (15). Finally, consistent with poor MHC expression, splenocytes added to untreated controls did not proliferate and, as shown in FIG. 10B, the cells remained in a quiescent state despite resting directly over the surface of the proliferating cancer cells.

Figure 10C:
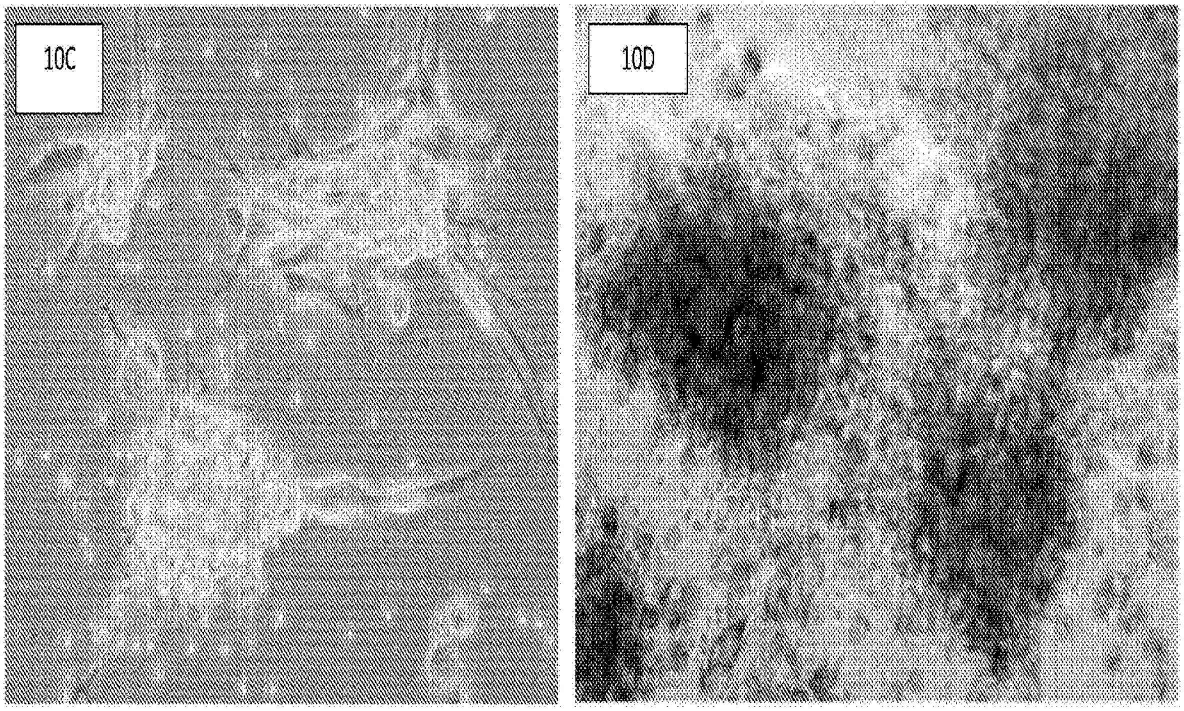
Figure 11A:
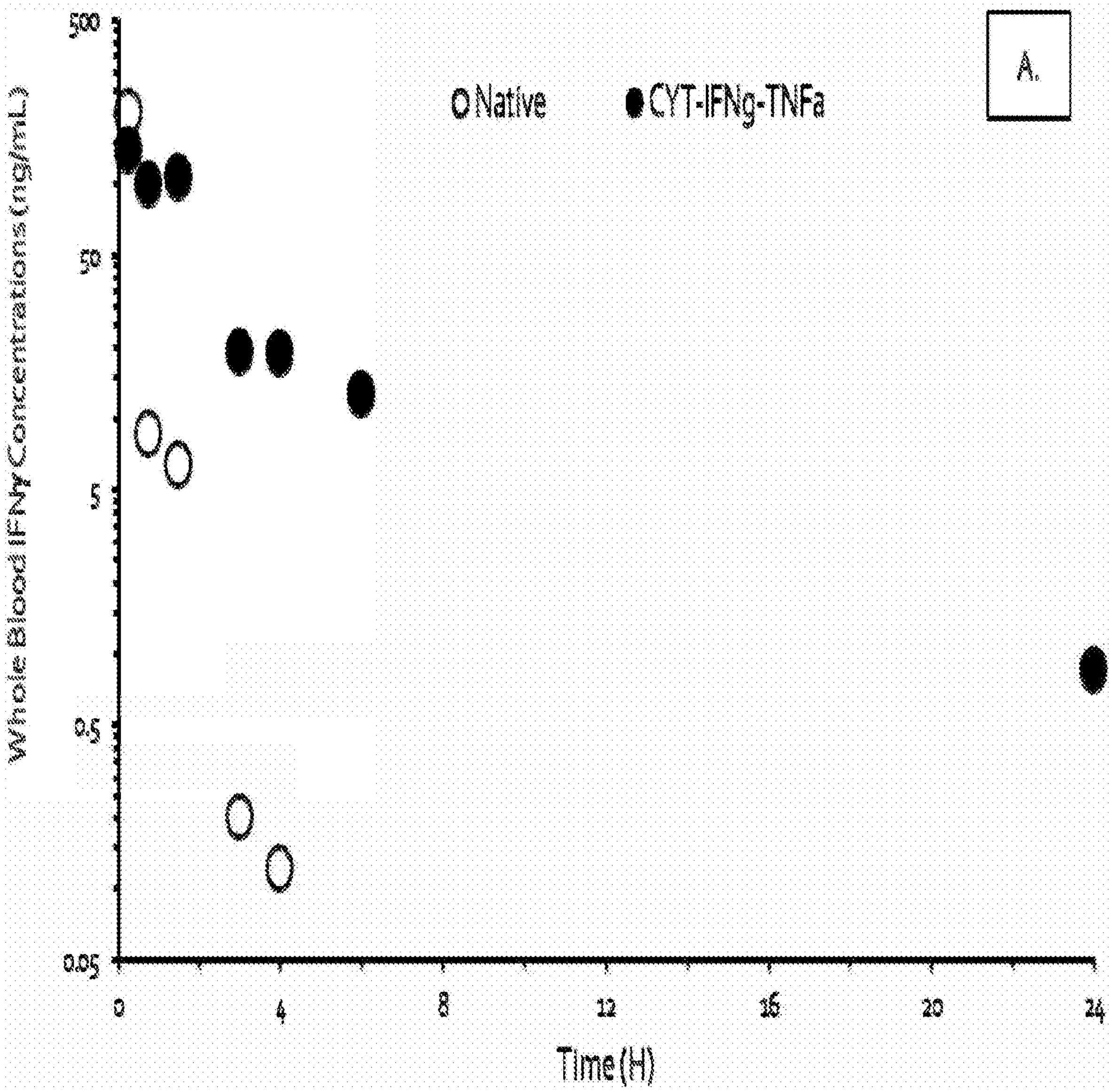
FIGS. 11A-11D provide plots showing CYT-IFNγ-TNFα increases blood residence time for both IFNγ and TNFα following an intraperitoneal injection (FIGS. 11A-11B) and intravenous injection (FIG. 11C-11D).
Figure 11B:
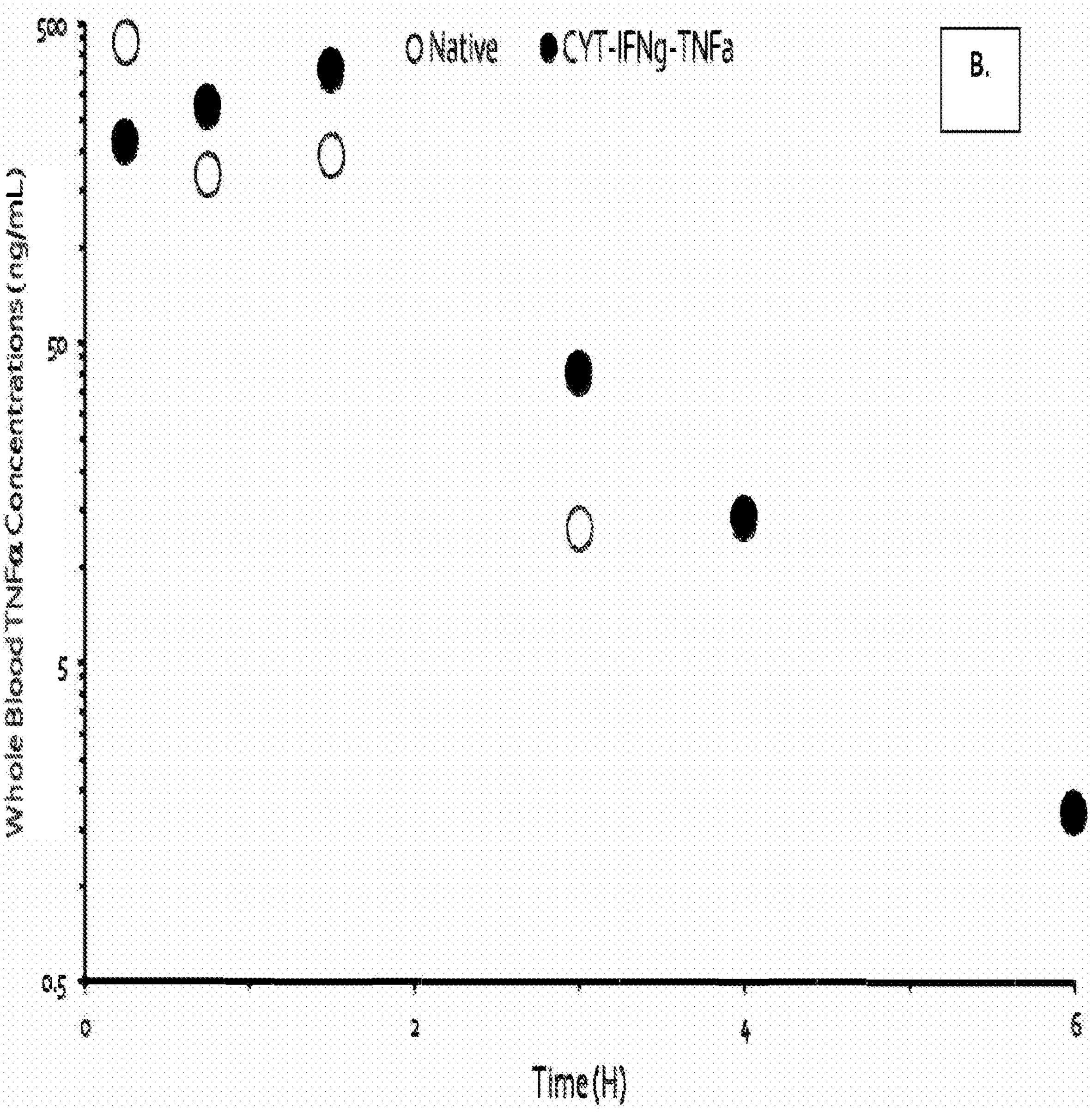
Figure 11C:
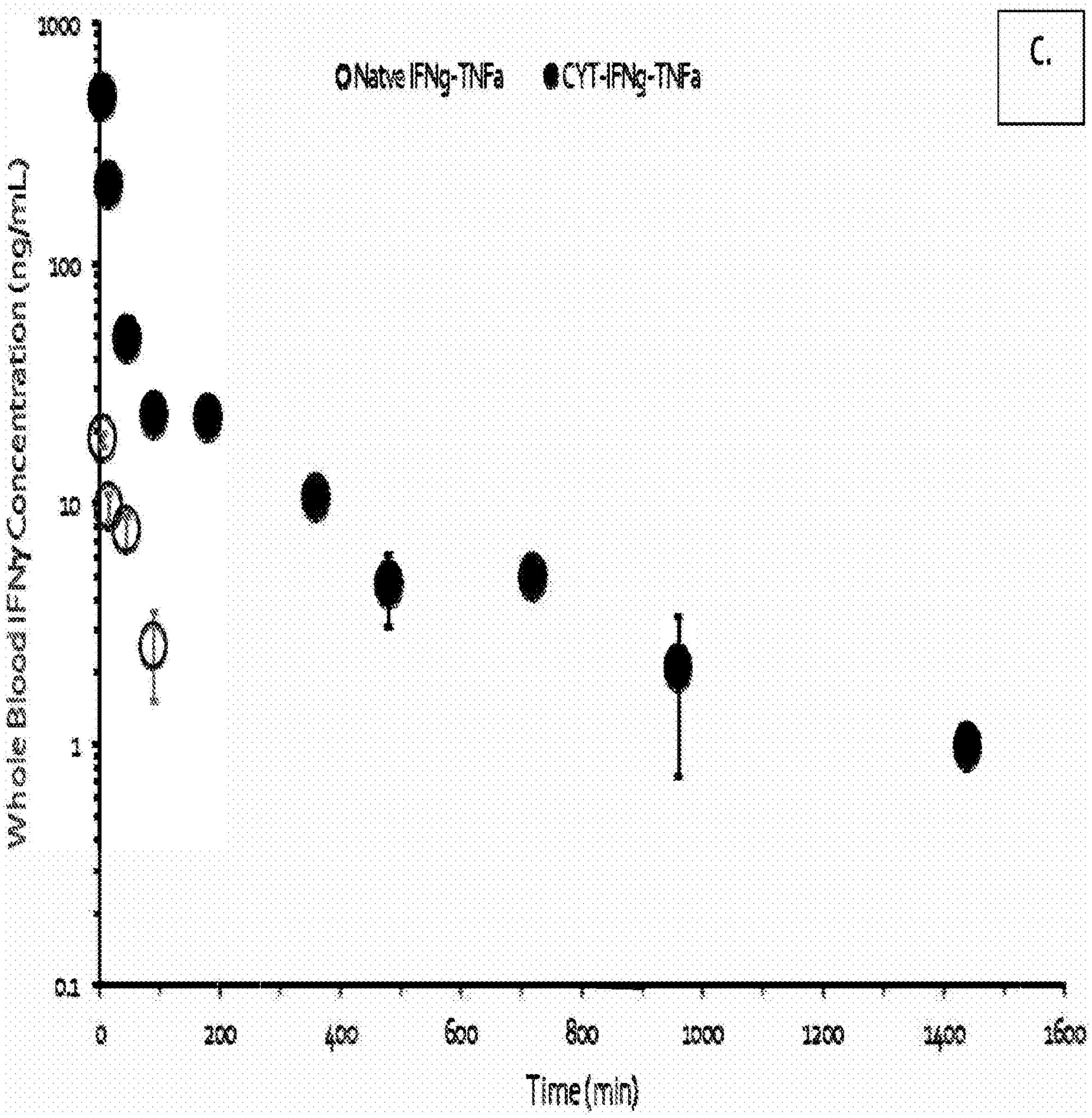
Figure 11D:
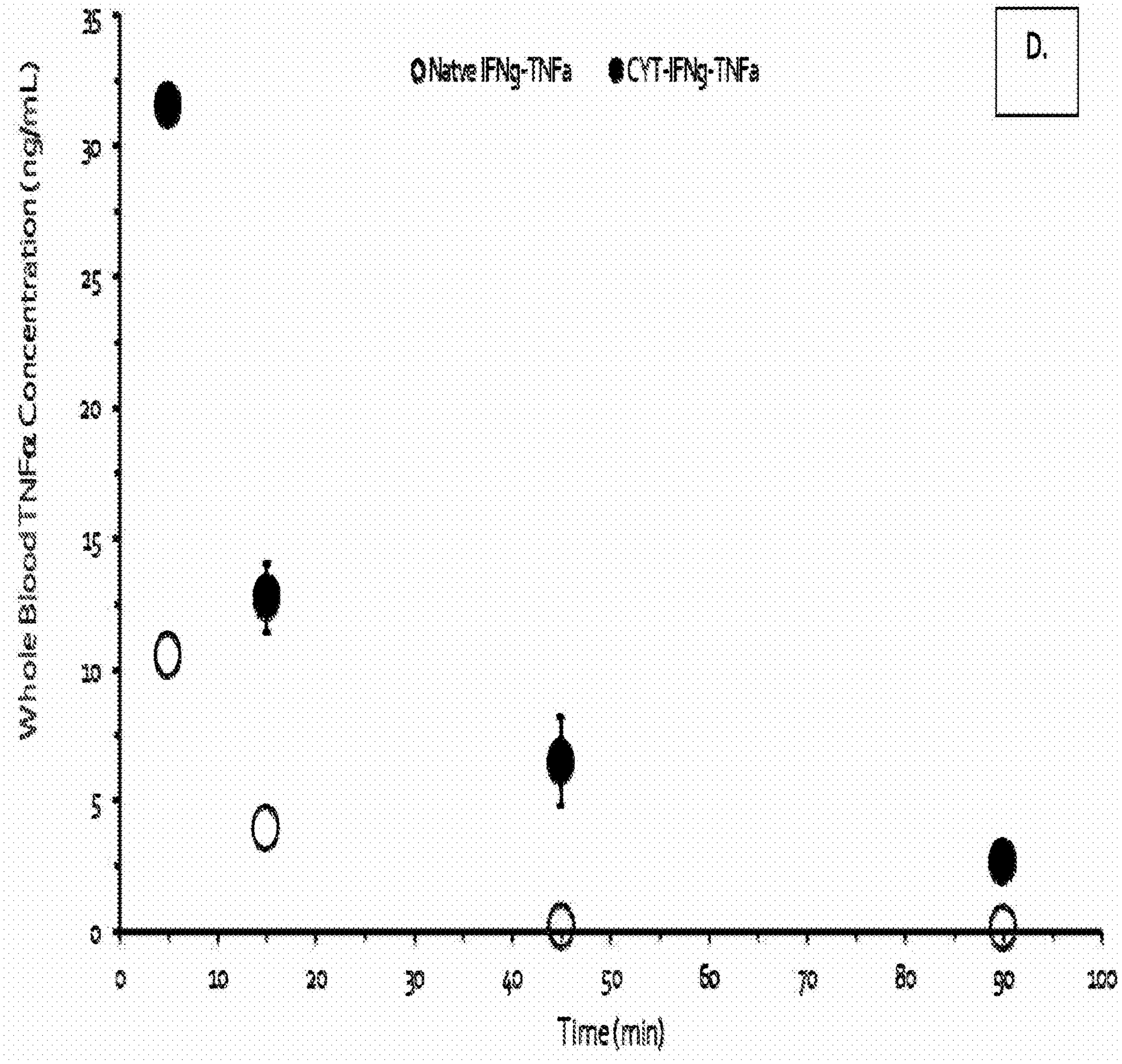

Similar data were obtained in CYT-mIFNγ-hTNFα treated B16F10 cancer cell cultures. As shown in FIG. 10C lymphocyte proliferation was evident within 24 hours of adding naïve splenocytes isolated from naïve C57Bl/6 to the CYT-mIFNγ-hTNFα-treated B16F10 melanoma cells. These data further support that in these studies, the nanoparticle resulted in antigen presentation by the cancer cells that ultimately led to lymphocyte proliferation.

Example 4

Pharmacology of CYT-IFNγ-TNFα

CYT-6091 (11-12) and CYT-21625 (16) are tumor targeting nanoparticles that target the delivery of TNFα, as a single agent (CYT-6091) or TNFα plus a paclitaxel prodrug (CYT-21625) to solid tumors. Both nanoparticles are engineered on 27 nm particles of PEGylated colloidal gold. Pharmacokinetic and tumor uptake studies reveal that CYT-6091 and CYT-21625, by virtue of PEGylation, increase pharmacokinetic exposure, as measured by terminal half-life ($T_{1/2}$) and Area Under the Curve (AUC), when compared to native preparations (11 and 16).

In the following experiments, the ability of the particle bound PEG-THIOL moiety to similarly increase pharmacokinetic exposure and tumor uptake of IFNγ was evaluated. Thus, after compounding and analytical interrogation of the nanoparticle, both TNFα and IFNγ in a single solution or the same dose of cytokines formulated as CYT-IFNγ-TNFα were injected into naïve or Colo-26 tumor-burdened Balb/c mice. Given that the currently approved form of IFNγ is injected subcutaneously, the PK profile was determined by injecting the drugs either intravenously or intraperitoneally.

At various times after the injection, the animals were sacrificed and whole blood was collected and spiked (10% v/v) with an 18 mg/mL solution of EDTA. The samples were measured for both TNFα and IFNγ content by a cytokine specific ELISA. To demonstrate that CYT-IFNγ-TNFα remained stable in the circulation, blood samples were collected after injection and analyzed using the XAb assay described in Example 1.

The data presented in FIG. 11 demonstrate that CYT-IFNγ-TNFα, increases pharmacokinetic exposure to both cytokines when compared to native cytokine treatment. These data are consistent with the pharmacokinetic profiles reported for both CYT-6091 and CYT-21625.

CYT-IFNγ-TNFα Does Not Undergo Burst Release Upon its Injection into the Circulation A common obstacle faced in nanoparticle development is burst release which refers to the near immediate release of the nanoparticle constituents upon injection. For both TNFα and IFNγ this may result in toxicity such as hypotension and may result in hepatotoxicity in the case of TNFα. Thus, to test the stability of CYT-IFNγ-TNFα in the circulation samples collected early in the pharmacokinetic study were analyzed in the cross-antibody (XAb) ELISA described in Example 1. Briefly, if either the TNFα or IFNγ constituents underwent burst release in the circulation one would predict that the blood samples would fail to generate a signal in the XAb ELISA as the particles would either not be captured or detected.

Figure 12:
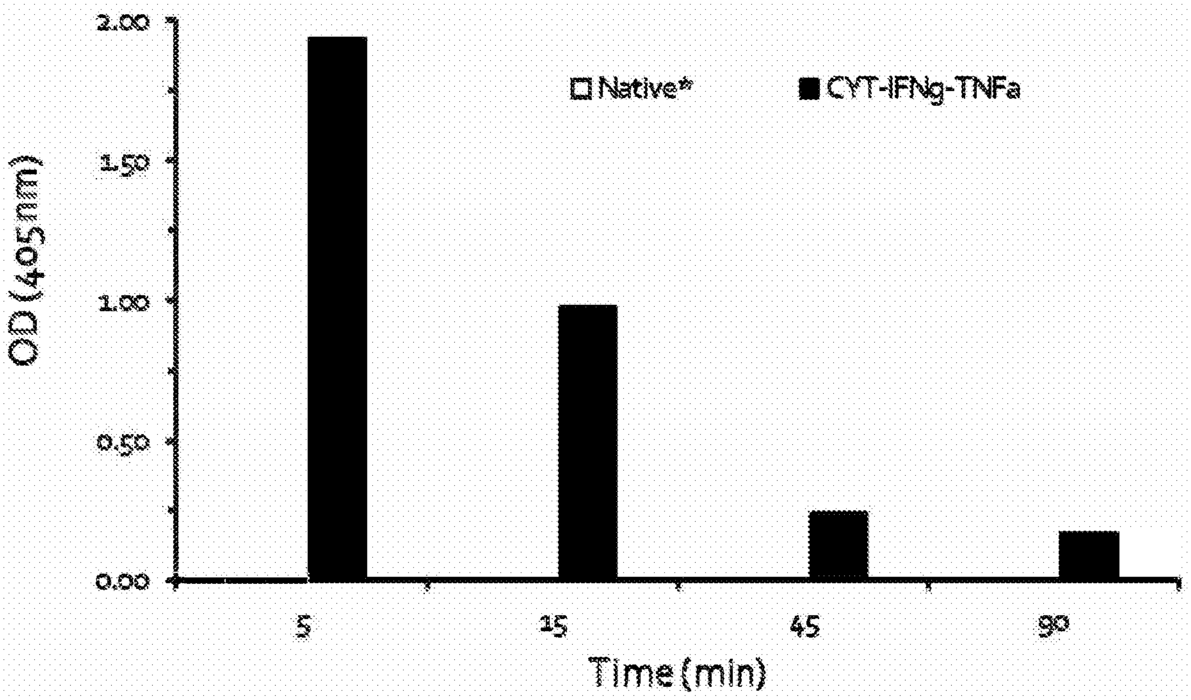
FIG. 12 provides a graph showing stability of CYT-IFNγ-TNFα in the circulation. Blood samples collected early in the pharmacokinetic study were analyzed in the cross-antibody ELISA described in Example 1. In this assay the samples were captured using a neutralizing monoclonal antibody against TNFα and detected with rabbit anti-human IFNγ/alkaline phosphatase conjugated goat anti-rabbit polyclonal antibodies.

The data presented in FIG. 12 support early-stage stability of the CYT-IFNγ-TNFα as the samples collected early in the pharmacokinetic study generated a significant signal in the XAb ELISA. Samples collected from animals receiving the native formulation did not generate significant signals in the ELISA.

Example 5

Accumulation of CYT-IFNγ-TNFα in Solid Tumors

Figure 13A:
FIGS. 13A and 13B provide images of experimental animals depicting visual confirmation of the uptake of CYT-mIFNγ-hTNFα by Colo-26 (solid) tumors. The presence of the gold nanoparticles was documented by digital photography of the mice 4 hours post injection. Colo-26 tumors acquired the reddish color of the gold nanoparticles (compare FIGS. 13A and 13B).
Figure 13B:

In the following study, the accumulation of the human or murine form of CYT-IFNγ-TNFα in two murine tumor models was tracked. In the first study, the presence of the nanoparticle was tracked by imaging control or nanoparticle treated animals. In FIG. 13, CYT-mIFNγ-hTNFα was intravenously injected into Colo-26 tumor burdened Balb/c mice. 3-4 hours post injection the presence of the nanoparticle was easily documented as the Colo-26 tumors acquired the reddish color of the gold nanoparticles (see FIGS. 13A and 13B).

Shown in FIG. 13A is image taken from a control (e.g., untreated) Colo-26 tumor-burdened Balb/c mouse. Shown in FIG. 13B is an image of a Colo-26 tumor burdened Balb/c mouse taken 3.5 hours after the mice received an intravenous injection of CYT-mIFNγ-TNFα. The accumulation of the CYT-mIFNγ-TNFα nanomedicine in the tumor was readily apparent as the tumor acquired the reddish color of the gold nanoparticles.

Accumulation of CYT-IFNγ-TNFα in B16F10 Tumors

For this study B16F10 tumors were established on the ventral surface of C57Bl/6 mice as described in Paciotti et. al. (14). Once the tumors were established mice (n=5/group) received an intraperitoneal injection of CYT-IFNγ-TNFα or the same cytokine dose administered in solutions. The animals were sacrificed 4 hours later and the tumors harvested and frozen at −80° C. The samples were later homogenized using a glass homogenizer. The homogenates were analyzed for intra-tumor IFNγ content by ELISA.

Figure 14:
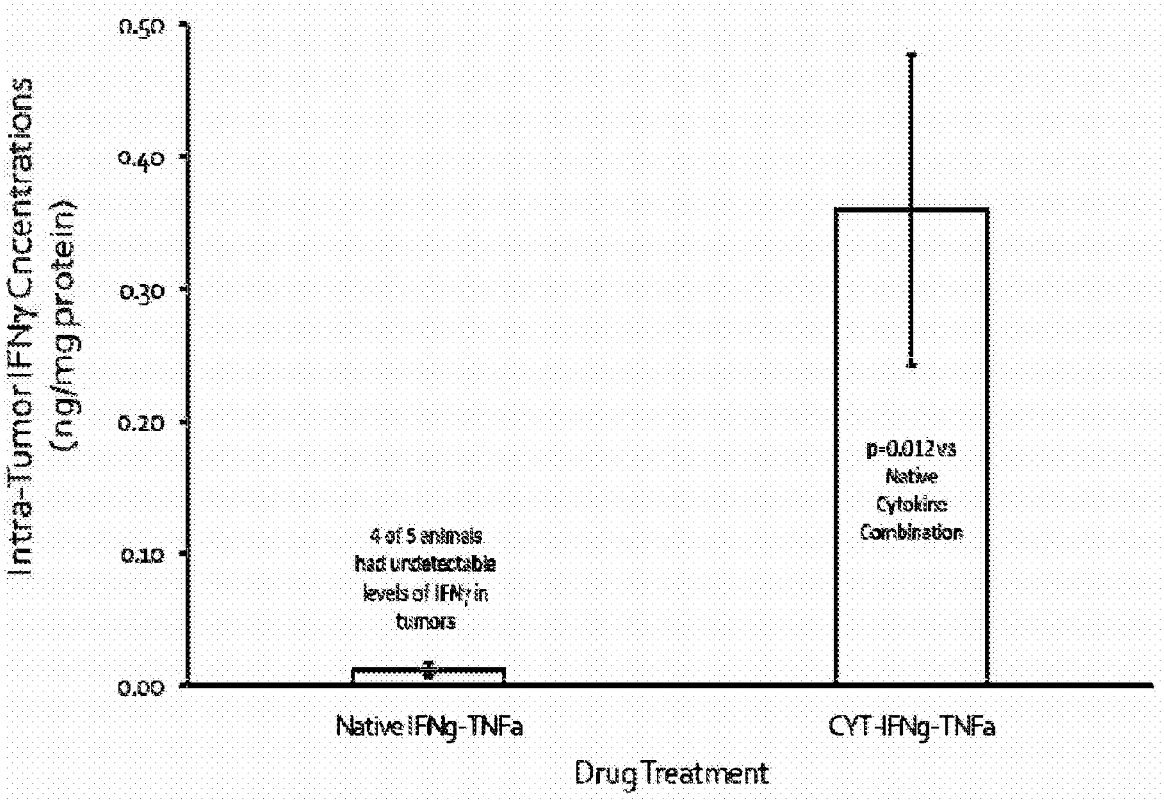
FIG. 14 provides a graph showing the accumulation of CYT-IFNγ-TNFα in B16F10 tumors.

Consistent with the data reported for CYT-6091 (10) and CYT-21625 (14), the data shown in FIG. 14 support that the nanoparticle accumulated IFNγ in solid tumors.

Example 6

Saturation Binding of Interleukin-2 or Interleukin-12: Generation of CYT-Interleukin-12 (CYT-IL-12) and CYT-Interleukin-2 (CYT-IL-2).

The data presented in the previous examples support that binding highly potent immune molecules such as INFγ and TNFα to the surface of PEGylated gold nanoparticles increases the potency of the cytokine(s) and improves their pharmacokinetic profiles to favor accumulation in solid tumors.

Using the methods described in Example 1, the development of additional follow-on nanoparticles with the potential of inducing and driving potent anti-cancer vascular and immune responses was pursued. Once manufactured, the nanoparticles were interrogated using the analytical methods described above.

Saturation binding curves were conducted for Interleukin-2 (IL-2) or Interleukin-12 (IL-12) by adding increasing amounts of the cytokine to a fixed volume of gold. After a 1-hour incubation, the particles were centrifuged at 14000 rpm and the supernatant was collected and set aside. The particles were reconstituted to 0.1× of their original volume and both the particle bound and free (supernatant) fractions were assayed by in-house IL-2 or IL-12 ELISAs.

Figure 15:
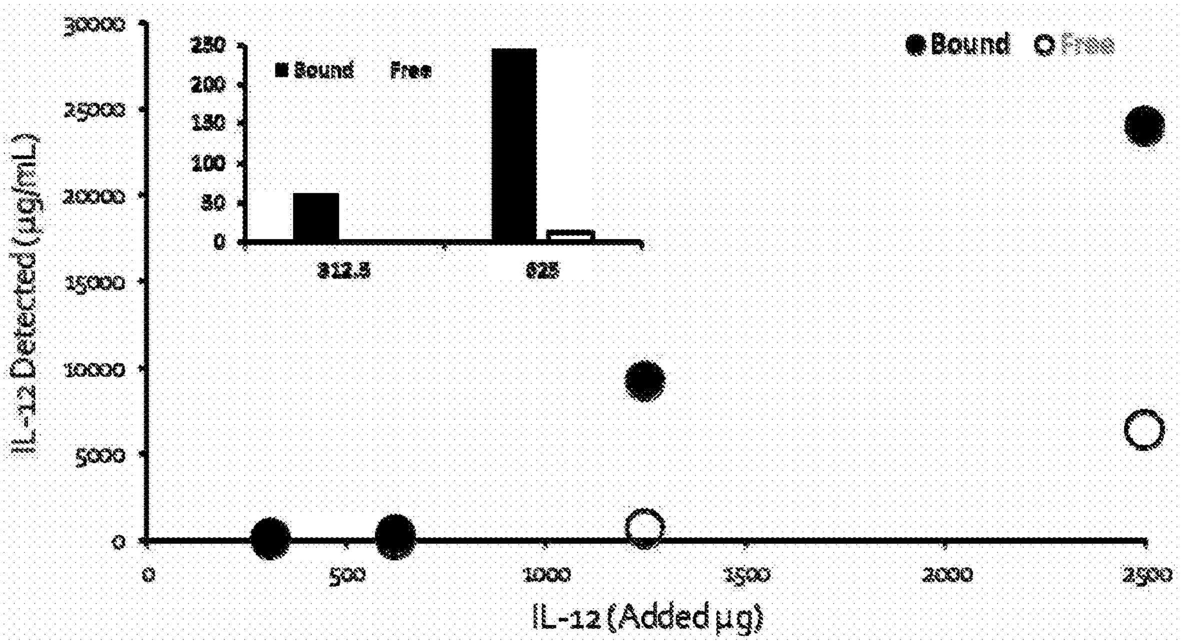
FIG. 15 illustrates the saturation binding kinetics of IL-12 to the colloidal gold nanoparticles.

The data shown in FIG. 15 show that IL-12 exhibited saturation binding for the gold particles. At relatively low masses, most of the cytokine was associated with the particles (filled circles). As the surface of the particles became saturated with the cytokine, more of it was detected as free (open circles).

Example 7

Formation of the Construct CYT-IL-12-TNFα Significantly Increases the Potency of IL-12.

Figure 16:
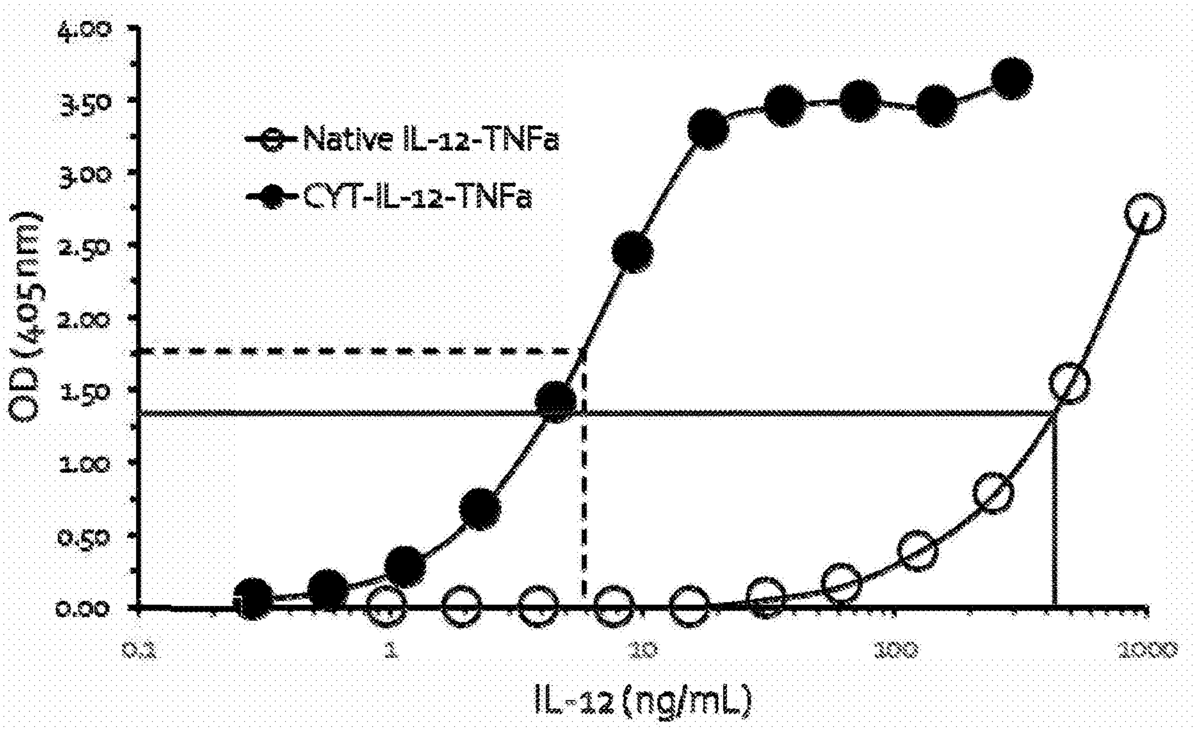
FIG. 16 provides a graph showing the increase in potency of CYT-IL-12-TNFα versus the same concentrations of native IL-12 plus TNFα in solution. The assay was performed using HEK-IL-12 cells, which like the HEK-IFNg cells secrete an alkaline phosphatase reporter protein.

Adopting the method described in Example 1 a dual agent IL-12-TNFα designated, CYT-IL-12-TNFα was manufactured. The potency of CYT-IL-12-TNFα was tested using a HEK-12 bioassay. Similar to the HEK-IFNγ cells, the HEK-IL-12 cells respond to IL-12 by secreting the same alkaline phosphatase reporter protein. Thus, for this study, equal doses of either native IL-12 or CYT-IL-12 were incubated with the HEK-IL-12 cells per the manufacturer's instructions. 48 hours later, a 10 μL sample from each of the replicate wells was added to 200 μL of the PNPP substrate. Similar to the data reported for the CYT-IFNγ-TNFα nanomedicine, CYT-IL-12-TNFα induced a significant increase in the potency of IL-12, which was nearly 70-fold higher (FIG. 16).

Example 8

Generation of an IL-2-TNF Dual Agent Nanoparticle

In the next series of studies, 5 μg of Interleukin-2 (IL-2), 0.25 μg of TNF and 15 μg PEG-THIOL were introduced to a single solution of gold nanoparticles. Single agent controls containing only one of the cytokines were also generated. Bound and free cytokine fractions were isolated by centrifugation. To demonstrate the presence of both cytokines on the same particle, single agent and dual agent nanoparticles were serially diluted and tested in both forms of the cross-antibody ELISA. For these assays, the dual or single agent nanoparticles were captured using either a TNFα or IL-2 monoclonal antibody. The monoclonal antibody captured material was detected using the rabbit polyclonal antibodies (Cytimmune Sciences, Inc. Maryland, USA) utilizing alkaline phosphatase conjugated goat-anti-rabbit to detect the complimentary cytokine.

Figure 17A:
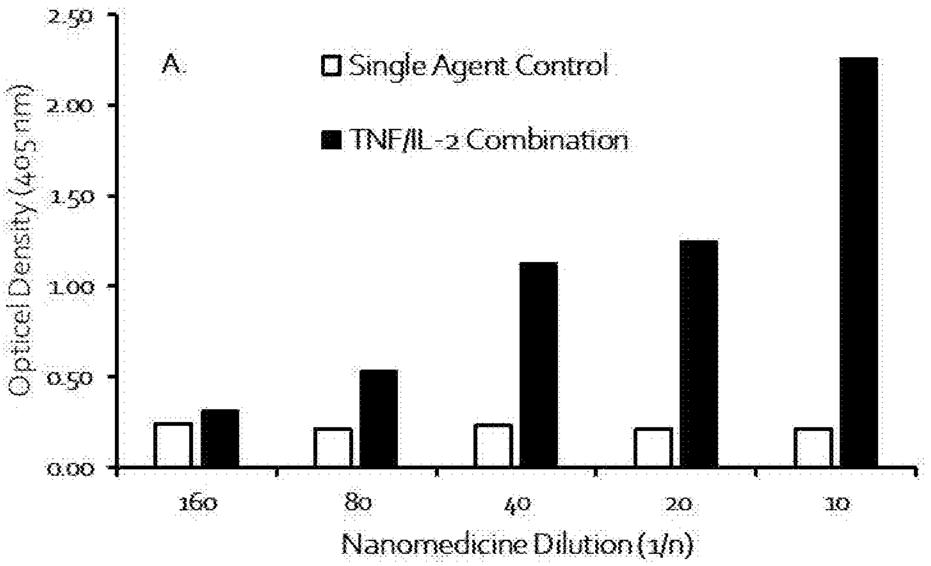
FIG. 17A and FIG. 17B present confirmatory data on the presence of human IL-2 and TNFα on the same particle of CYT-IL-2-TNFα.
Figure 17B:
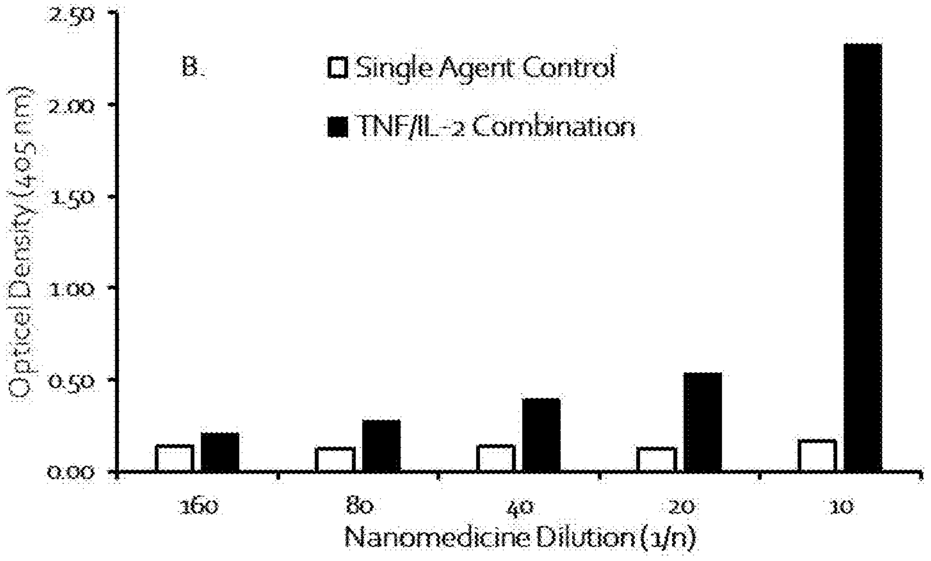

The data presented in FIG. 17 confirm the presence of both cytokines on the same particle. In both assays, the single agent controls generated minimal color, whereas the dual agent particles generated clear signals above the signal generated by single agent controls. Furthermore, the amplitude of signals generated in each XAb ELISA were consistent with the amount of cytokine originally bound. For example, in the TNFα captured XAb assay, detecting IL-2 exhibited significant signals across the dilutional curve. Conversely, while a dilutional curve was observed in the IL-2 XAb assay, the TNFα signals exhibited a greater drop in signal for each dilution in the dilutional curve.

Example 9

Development of a Multimodal IO Nanoparticle

There exists long-standing evidence suggesting that many chemotherapies activate the immune system as part of their anti-tumor efficacy (17-18). Conceptually, chemotherapy may generate the cancer antigens needed to initiate and drive cancer immunotherapy. This is supported by the fact that many of the current clinical trials focused on immuno-oncology have added a chemotherapy arm (19-20). Other therapies including precision medicines have the potential to restore or block biologic pathways that could enhance or drive anti-cancer efficacy in combination with cytokines and to those ends there is an increasing list of small molecule immuno-oncology drugs that are in development.

Figure 18:
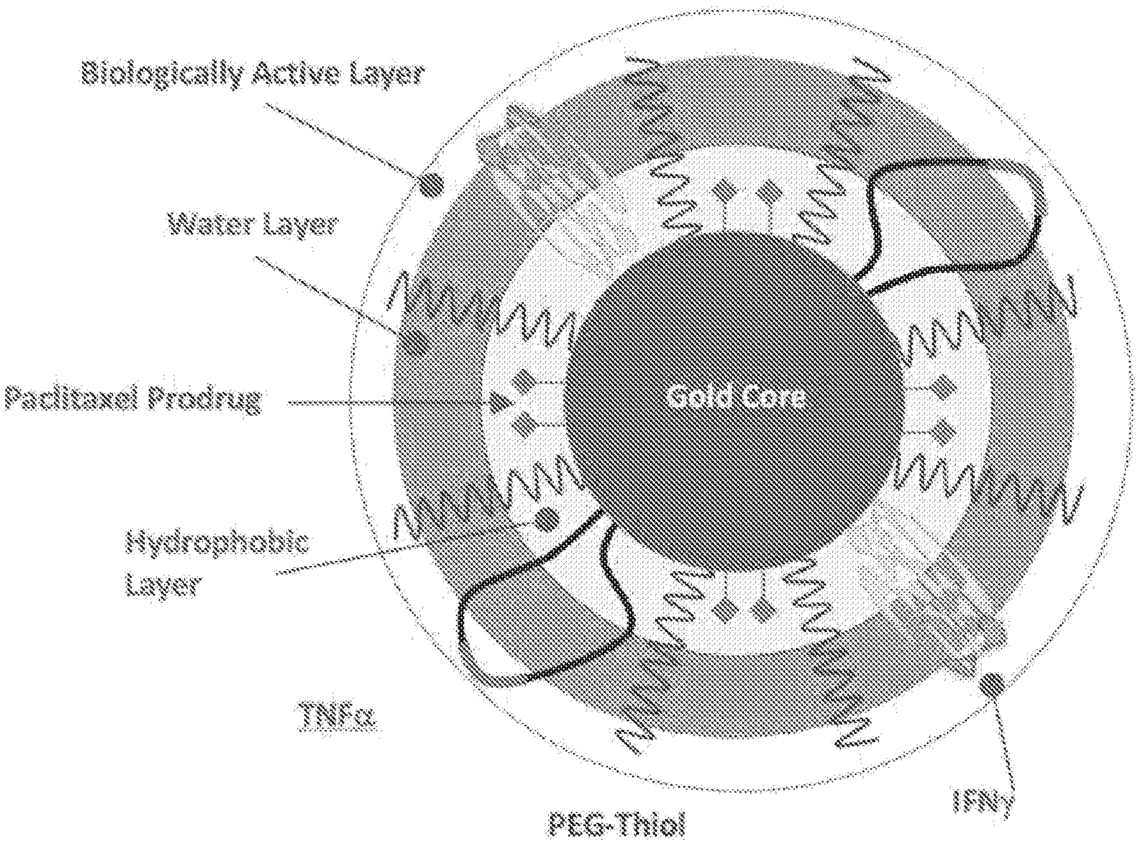
FIG. 18 provides a schematic of a multimodal immuno-oncology nanoparticle. The novel nanoparticles consist of human IFNγ, human TNFα and a thiolated paclitaxel prodrug that are bound to the same gold nanoparticle.

To demonstrate the ability to generate such drugs a multimodal immuno-oncology nanoparticle comprised of both TNFα and IFNγ was developed, to which a small molecule prodrug was added. A schematic of the new nanoconstruct is shown in FIG. 18. Specifically, we bound a previously described thiol derivatized prodrug form of paclitaxel to the existing CYT-IFNγ-TNFα parent nanoparticle.

Using the methods outlined in Example 1, 2.5 μg of the thiolated paclitaxel analog was added to the existing formulation. Free drugs were separated from the particle bound constituents by centrifugation and the nanoparticle was analyzed for cytokine concentration.

To gain an initial understanding of the impact of adding the paclitaxel prodrug to CYT-IFNγ-TNFα FTC-133 cells were incubated with similar doses of IFNγ and TNFα added as either CYT-IFNγ-TNFα or CYT-IFNγ-TNFα-Paclitaxel nanoparticles. Significant morphologic changes were noted within two days of incubation. For example, for CYT-IFNγ-TNFα perinuclear localization of the particles, previously described, were observed. In the case of CYT-IFNγ-TNFα-Paclitaxel the nuclei became segmented with particles localized around each segment.

Figure 19:
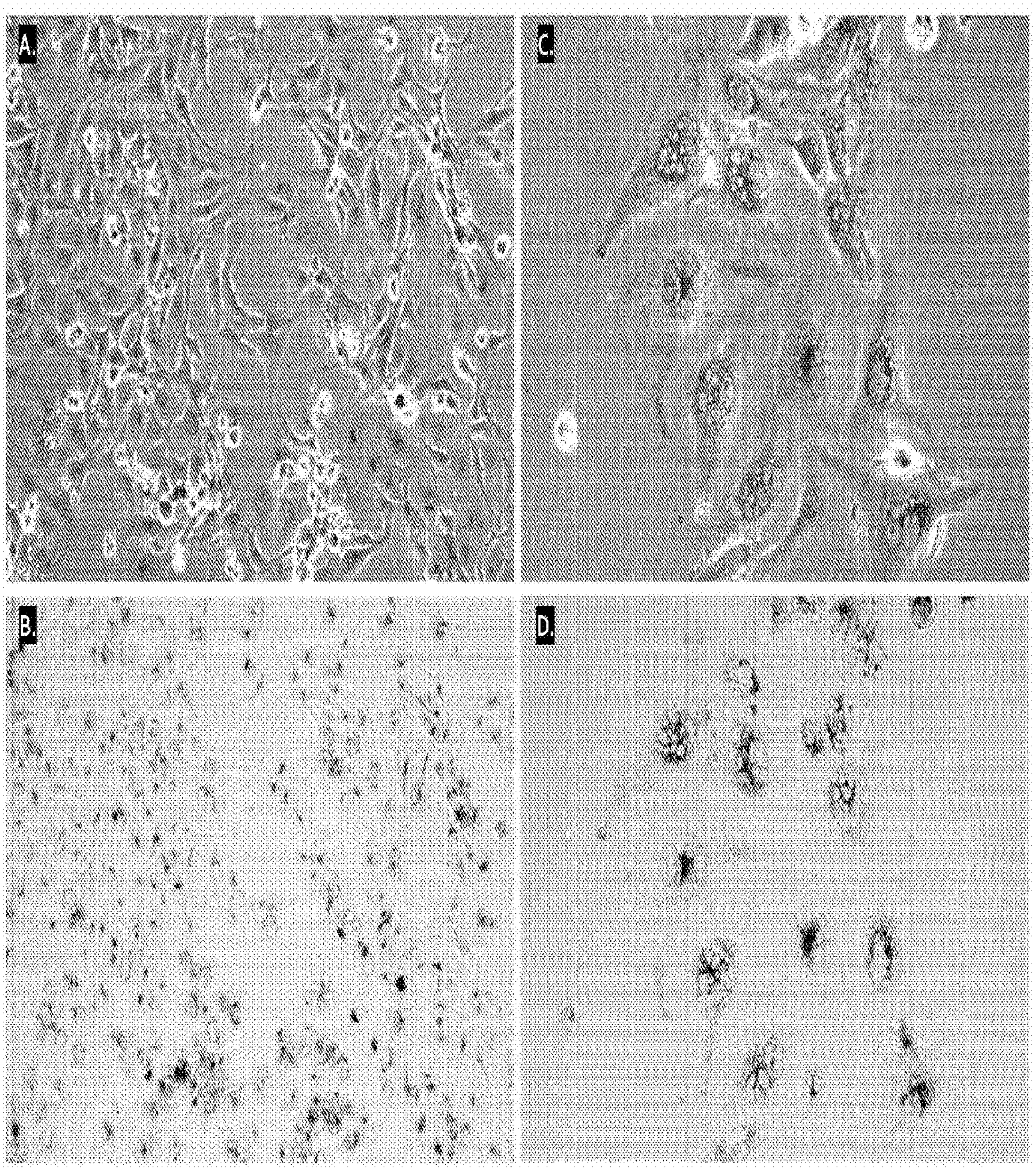
FIG. 19 provides micrographs comparing the uptake of CYT-IFNγ-TNFα vs CYT-IFNγ-TNFα-Paclitaxel by FTC-133 cells. The paclitaxel containing nanoparticle induced profound changes to the morphology of the nucleus that caused the formation of multi-segmented nuclei.

The micrographs presented in FIG. 19 illustrate that CYT-IFNγ-TNFα represent a unique mechanism for targeting the intracellular delivery of small molecule immune-oncology drugs with the TNFα and IFNγ. To further demonstrate this concept, a derivative nanoparticle where the thiolated paclitaxel prodrug was substituted with a fluorescently labelled 2 kDa form PEG-THIOL was generated. Adding this construct to FTC-133 cells enabled tracking of both the entry of the particles into the cell as well as the release of the prodrug surrogate (e.g., the fluorescently labelled 2 kDa form PEG-THIOL).

Figure 20:
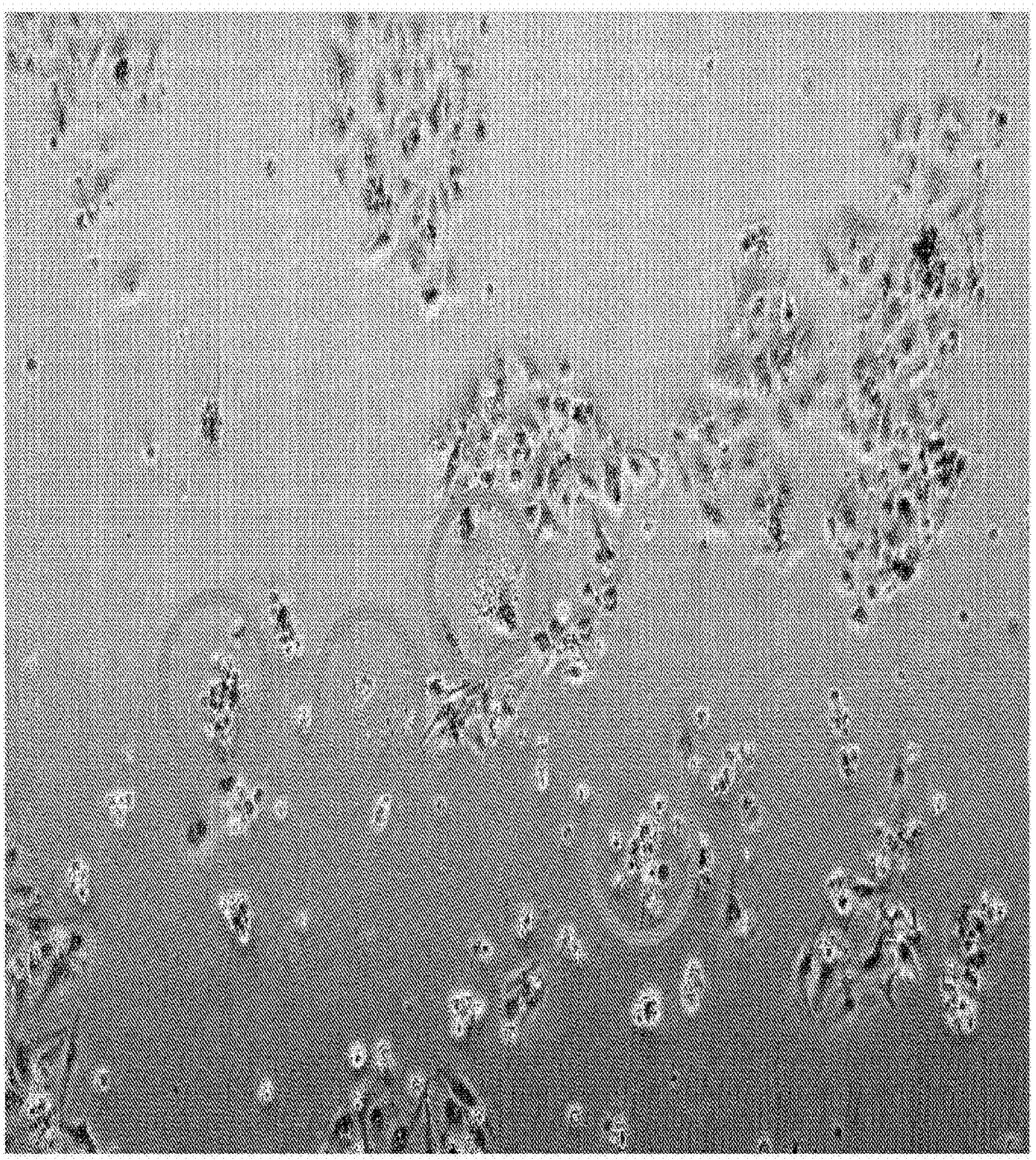
FIG. 20 provides a micrograph showing the mechanism CYT-IFNγ-TNFα-Paclitaxel may generate tumor antigens. Upon lysis the dead cells may release particles containing putative tumor antigens. In doing so the new construct may generate tumor antigens to initiate an anti-tumor immune response.

The nanoparticles discussed within this document suggest a possible treatment strategy for solid tumors. Shown in FIG. 20 are FTC-133 cells treated with CYT-IFNγ-TNFα-Paclitaxel. The treatment with CYT-IFNγ-TNFα-Paclitaxel results in the lysis of the cells and the generation of cellular fragments (highlighted by circles in FIG. 20). These cellular fragments may contain tumor antigens which may serve to initiate the immune response. These findings show that using CYT-IFNγ-TNFα-Paclitaxel to initiate the immune response followed by other immune-oncology nanoparticles would represent a possible treatment strategy to further drive the anti-tumor immune response.

Figure 21:
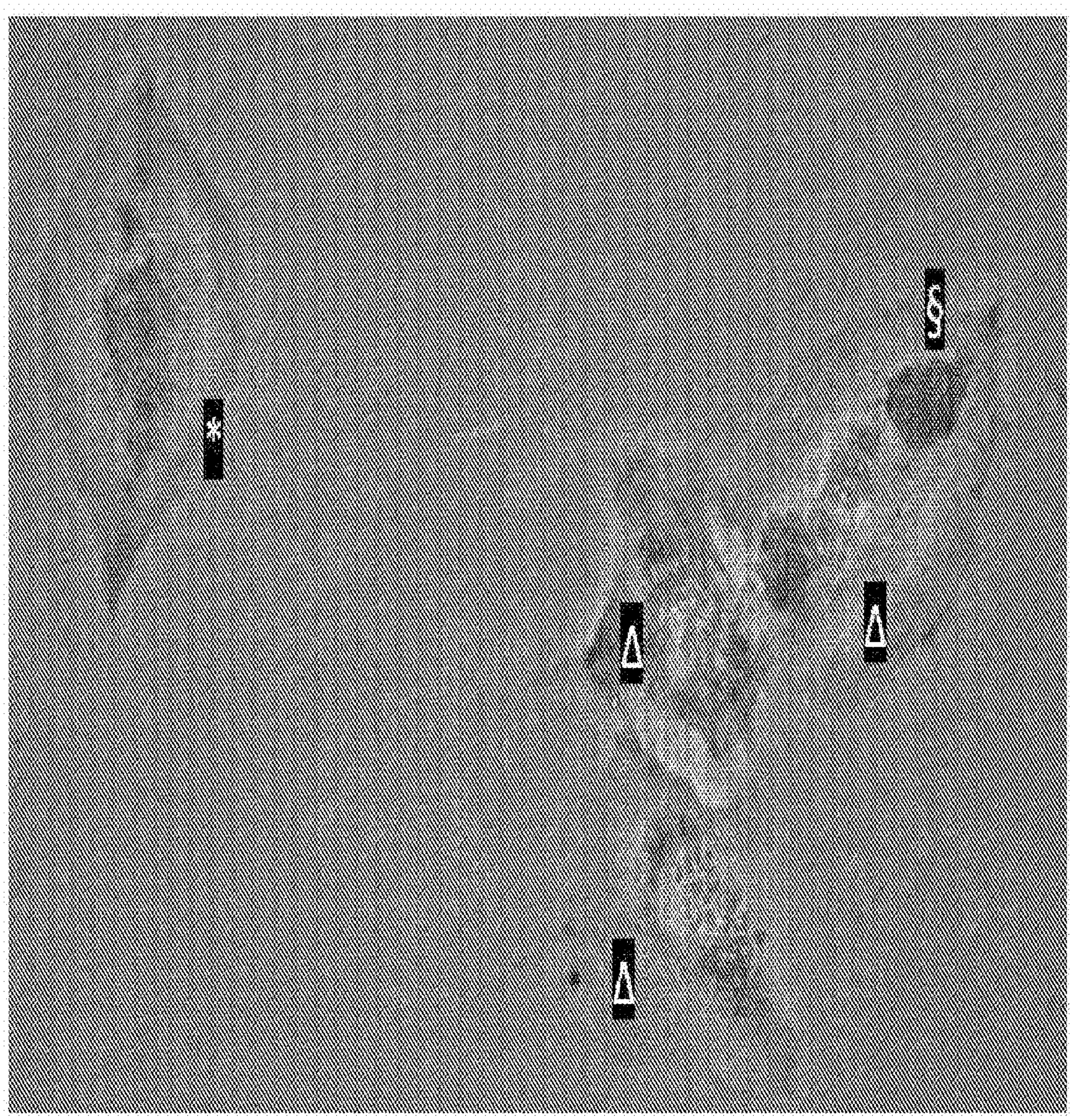
FIG. 21 provides a composite fluorescent/bright field image of FTC-133 cells treated with the CYT-IFNγ-TNFα-Paclitaxel construct. The intracellular trafficking of the particles was once again readily apparent by the red color of the particles (See §). Furthermore, as the nanoparticles arrive at the perinuclear region the fluorescent marker becomes apparent supporting the release of the prodrug (or small molecule payload). These data are consistent with the release of the prodrug surrogate from the particles (Δ). The image also portrays the post-internalization release of the surrogate active pharmaceutical ingredient (API) at different stages. For example, the release of the API is well underway in cells highlighted by the triangle (Δ). However, early-stage release is also shown in the cell designated by the star (*).

Shown in FIG. 21 is a composite fluorescent/bright field image of FTC-133 cells treated with this construct. The intracellular trafficking of the particles was evidenced by the red color of the particles (§). What is also apparent is that as the nanoparticles arrive at the perinuclear region the fluorescent marker becomes apparent supporting the release of the prodrug surrogate from the particles (Δ).

REFERENCES

1. Alexander, H. R., & Feldman, A. 2000. Tumor Necrosis Factor: Basic Principles and clinical applications in systemic and regional cancer treatment. In Principles and Practice of the Biologic Therapy of Cancer. Eds. S. Rosenberg. Lippincott Williams and Wilkins.
2. Lode, H. N., Xiang, R., Duncan, S. R., Theofilopoulos, A. N., Gillies, S. D., & Reisfeld, R. A. 1999. Tumor-targeted IL-2 amplifies T cell-mediated immune response induced by gene therapy with single-chain IL-12. Proc. Natl. Acad. Sci. USA. 96:8591.
3. Nagarajan, S., & Selvaraj, P. 2002. Glycolipid-anchored IL-12 expressed on tumor cell surface induces antitumor immune response. Cancer Res. 62, 2869.
4. FTC-133 cell line: For a description of the cell line please see https://www.sigmaaldrich.com/US/en/product/sigma/94060901?gclid=Cj0KCQjwn_OlBhDhARI sAG2y6zNT-b7BKWDWPBO6l6OjVUjNF0Vus40EnabHKjd ser6KPxowvAzmFegaAiSFEALw_wcB&gclsrc=aw.ds (last accessed Jul. 24, 2023)

5. Farma, J. M., Puhlmann, M., Soriano, P. A., Cox, D., Paciotti G. F., Tamarkin, L., Alexander, H. R. (2007). Direct evidence for rapid and selective induction of tumor neovascular permeability by tumor necrosis factor and a novel derivative, colloidal gold bound tumor necrosis factor. International journal of cancer. 120(11):2474-80.
6. Koonce, N. A., Quick, C. M., Hardee, M. E., Jamshidi-Parsian, A., Dent, J. A., Paciotti, G. F., Nedosekin, D., Dings-Ruud, P. M., Griffin, R. J. (2015). Combination of Gold Nanoparticle-Conjugated Tumor Necrosis Factor-a and Radiation Therapy Results in a Synergistic Antitumor Response in Murine Carcinoma Models. Int J Radiation OncolBiol Phys. 93(3):588.
7. Tamarkin., L., Yuan, Z., Maggi, E. C., Adem, A., Schorzman, A. N., Zamboni, W. C., Oarr, D. and Libutti, S. K. 2017. Cancer Nanomedicines: Opportunities and Challenges. TechConnect Briefs 2017: 126Libutti, S. K., Paciotti, G. F., Byrnes, A. A., Alexander, H. R., 1008 Gannon, W. E., Walker, M., Seidel, G. D., Yuldasheva, N., and 1009 Tamarkin, L. (2010) Phase I and pharmacokinetic studies of CYT-1010 6091, a novel PEGylated colloidal gold-rhTNF nanomedicine. Clin. 1011 Cancer Res. 16, 6139-6149.
8. Pfreundschuh et al., Phase I Study of Intratumoral Application of Recombinant Human Tumor Necrosis Factor. European Journal Cancer Clinical Oncology, Vol 25, No 2, pp. 379-388, 1989.
9. Ichikawa, Y., Ghanefar, M., Bayeva, M., Wu, R., Khechaduri, R., Prasad, S. V. N., Mutharasan, R. K., Naik, T. J., and Ardehalil, H. 2014. Cardiotoxicity of doxorubicin is mediated through mitochondrial iron accumulation. J Clin Invest. 124(2):617-630.
10. Fraker, D. L., Alexander, H. R., Andrich, M., and Rosenberg, S. A. 1996. Treatment of patients with melanoma of the extremity using hyperthermic isolated limb perfusion with melphalan, tumor necrosis factor, and interferon gamma: results of a tumor necrosis factor dose-escalation study. J. Clin. Oncol. 14:479-489.
11. Paciotti, G. F., Myer, L., Weinreich, D., Goia, D., Pavel, N., Mclaughlin, R. E., Tamarkin, L. (2004). Colloidal gold: a novel nanoparticle vector for tumor directed drug delivery. Drug delivery. 11(3):169-83.
12. Libutti, S. K., Paciotti, G. F., Byrnes, A. A., Alexander, H. R. Jr, Gannon, W. E., Walker, M, Seidel, G. D., Yuldasheva, N., Tamarkin, L. (2010). Phase I and pharmacokinetic studies of CYT-6091, a novel PEGylated colloidal gold-rhTNF nanomedicine. Clinical Cancer Research. 6(24):6139-49.
13. Zhour, G. 2009. Molecular mechanisms of IFN-gamma to up-regulate MHC class I antigen processing and presentation. Int Rev Immunol. 28(3-4):239-60
14. Angell, T. E., Lechner, M. G., Jang, J. K., LoPresti, J. S. and Epstein, A. L. 2014. MHC Class I Loss Is a Frequent Mechanism of Immune Escape in Papillary Thyroid Cancer That Is Reversed by Interferon and Selumetinib Treatment In Vitro. Clin. Can. Res. 20:6034-6044.
15. Paciotti, G. F., Raghunadan, R., Huhta, M. S. and Tamarkin. 2011. Compositions and methods for generating antibodies. USPTO. U.S. Pat. No. 8,486,663B2.
16. Paciotti G. F., Zhao, J., Cao, S., Brodie, P. J., Tamarkin, L., Huhta, M., Myer, L., Friedman, J., Kingston, D. G. I. (2016). Synthesis and Evaluation of Paclitaxel-Loaded Gold Nanoparticles for Tumor-Targeted Drug Delivery. Bioconjug Chem. 27(11):2646-2657.
17. Emens, L. A. 1011. Chemotherapy and tumor immunity: an unexpected collaboration. Front Biosci.; 13:249-257.
18. Zitvogel, L., Apetoh, L., Ghiringhelli, F., and Kroemer. 2008. Immunological aspects of cancer chemotherapy. Nature Immune. 8:59-73.
19. Ning, N., Yu, Y., Shao, S., Deng, R., Yu, J., Wang, X., She, X., Huang, D., Shen, X., Duan, W., Duan, J., Zhang, H. 2021. The prospect of immunotherapy combined with chemotherapy in patients with advanced non-small cell lung cancer: a narrative review. Annals of Translational Medicine. 9:1703
20. Zhu, S., Zhang, T., Zheng, L., Liu, H., Song, W., Liu, D., Li, Z., and Pan, C. X. 2021. Combination strategies to maximize the benefits of cancer immunotherapy. J Hematol. Oncol. 14:156

The invention claimed is:

1. A composition comprising a gold nanoparticle bound to a first cytokine and a second cytokine, wherein the first cytokine comprises Tumor Necrosis Factor alpha (TNFα), and wherein the second cytokine comprises Interferon gamma (IFNγ).

2. The composition of claim 1, wherein a ratio of TNFα to IFNγ, by weight, is 20:1.

3. The composition of claim 1, wherein the gold nanoparticle is covalently bound to the first cytokine and the second cytokine.

4. The composition of claim 1, wherein the gold nanoparticle is covalently bound to the first cytokine via a first thiol group and the gold nanoparticle is covalently bound to the second cytokine via a second thiol group.

5. The composition of claim 1, further comprising a polyethylene glycol, a polyethylene glycol derivative, or a polyethylene glycol-thiol.

6. The composition of claim 1, further comprising paclitaxel, a paclitaxel analogue, or a paclitaxel prodrug.

7. The composition of claim 1, wherein a ratio of TNFα to IFNγ, by weight, is 18:1 to 22:1.

8. The composition of claim 1, wherein a size of the gold nanoparticle is about 27 nm.

9. The composition of claim 1, further comprising a polyethylene glycol-thiol, wherein a size of the polyethylene glycol-thiol is 2 kDa to 20 kDa.

10. The composition of claim 1, wherein the first cytokine and/or the second cytokine are bound to the gold nanoparticle using ionic binding.

11. The composition of claim 1, wherein the first cytokine and/or the second cytokine are bound to the gold nanoparticle using hydrophobic interactions.

12. A composition comprising a gold nanoparticle, wherein the gold nanoparticle is bound to a first cytokine and a second cytokine, wherein the first cytokine consists of Tumor Necrosis Factor alpha (TNFα), and wherein the second cytokine consists of Interferon gamma (IFNγ).

13. The composition of claim 12, wherein a ratio of TNFα to IFNγ, by weight, is 20:1.

14. The composition of claim 12, wherein a ratio of TNFα to IFNγ, by weight, is 18:1 to 22:1.

15. The composition of claim 12 wherein the gold nanoparticle is covalently bound to the first cytokine and the second cytokine.

16. The composition of claim 12, further comprising a polyethylene glycol, a polyethylene glycol derivative, or a polyethylene glycol-thiol.

17. The composition of claim 12, further comprising a polyethylene glycol-thiol, wherein a size of the polyethylene glycol-thiol is 2 kDa to 20 kDa.

18. The composition of claim 12, further comprising paclitaxel, a paclitaxel analogue, or a paclitaxel prodrug.

19. The composition of claim 12, wherein a size of the gold nanoparticle is about 27 nm.

20. The composition of claim 1, wherein the first cytokine and/or the second cytokine are bound to the gold nanoparticle using ionic binding or hydrophobic interactions.

* * * * *